(12) United States Patent
Kawai et al.

(10) Patent No.: US 8,802,105 B2
(45) Date of Patent: Aug. 12, 2014

(54) ANTIBACTERIAL COMPOSITIONS

(71) Applicant: Forsyth Dental Infirmary for Children, Cambridge, MA (US)

(72) Inventors: Toshihisa Kawai, Brookline, MA (US); Philip P. Stashenko, Medfield, MA (US); Yoshitaka Hosokawa, Tokushima (JP); Kazuhisa Ohara, Hiroshima (JP)

(73) Assignee: Forsyth Dental Infirmary for Children, Cambridge, MA (US)

( * ) Notice: Subject to any disclaimer, the term of this patent is extended or adjusted under 35 U.S.C. 154(b) by 8 days.

(21) Appl. No.: 13/795,972

(22) Filed: Mar. 12, 2013

(65) Prior Publication Data

US 2013/0303619 A1 Nov. 14, 2013

Related U.S. Application Data

(62) Division of application No. 12/762,234, filed on Apr. 16, 2010, now Pat. No. 8,399,220.

(60) Provisional application No. 61/169,845, filed on Apr. 16, 2009.

(51) Int. Cl.
*A61K 31/00* (2006.01)
*A61K 31/185* (2006.01)
*A61K 39/00* (2006.01)

(52) U.S. Cl.
USPC .............................. 424/184.1; 514/1; 514/576

(58) Field of Classification Search
None
See application file for complete search history.

(56) References Cited

U.S. PATENT DOCUMENTS

| | | |
|---|---|---|
| 3,535,421 A | 10/1970 | Briner et al |
| 3,538,230 A | 11/1970 | Pader et al |
| 3,678,154 A | 7/1972 | Widder et al. |
| 3,689,637 A | 9/1972 | Pader |
| 3,696,191 A | 10/1972 | Weeks |
| 3,711,604 A | 1/1973 | Colodney et al. |
| 3,862,307 A | 1/1975 | Di Giulio |
| 3,911,104 A | 10/1975 | Harrison |
| 3,935,306 A | 1/1976 | Roberts et al. |
| 3,937,807 A | 2/1976 | Haefele |
| 3,959,458 A | 5/1976 | Agricola et al. |
| 3,991,177 A | 11/1976 | Vidra et al. |
| 4,040,858 A | 8/1977 | Wason |
| 4,051,234 A | 9/1977 | Gieske et al. |
| 4,058,595 A | 11/1977 | Colodney |
| 4,154,815 A | 5/1979 | Pader |
| 4,172,124 A | 10/1979 | Koprowski et al. |
| 4,340,583 A | 7/1982 | Wason |
| 4,355,022 A | 10/1982 | Rabussay |
| 4,612,132 A | 9/1986 | Wollenberg et al. |
| 4,842,847 A | 6/1989 | Amjad |
| 4,866,161 A | 9/1989 | Sikes et al. |
| 4,992,420 A | 2/1991 | Neeser |
| 5,000,939 A | 3/1991 | Dring et al. |
| 5,004,597 A | 4/1991 | Majeti et al. |
| 5,358,713 A | 10/1994 | Shimamura |
| 5,643,873 A | 7/1997 | Barrett et al. |
| 5,654,276 A | 8/1997 | Barrett et al. |
| 6,149,894 A | 11/2000 | Yamane et al. |
| 6,500,409 B1 | 12/2002 | Scherl et al. |
| 7,416,854 B2 | 8/2008 | Riss et al. |
| 2002/0098248 A1 | 7/2002 | Fujiwara et al. |
| 2006/0057134 A1 | 3/2006 | Kirikae et al. |
| 2006/0134286 A1 | 6/2006 | Maeda |
| 2006/0141073 A1 | 6/2006 | Worrell et al. |
| 2010/0330070 A1 | 12/2010 | Kawai et al. |

FOREIGN PATENT DOCUMENTS

| | | |
|---|---|---|
| EP | 0415126 A1 | 3/1991 |
| EP | 0443090 A2 | 8/1991 |
| EP | 1504754 A1 | 2/2005 |
| EP | 1724359 A1 | 11/2006 |
| JP | 2025413 | 1/1990 |
| JP | 9194358 | 7/1997 |
| JP | 11246599 | 9/1999 |
| JP | 2002212090 A | 7/2002 |
| KR | 20090104955 A | 10/2009 |
| WO | WO-0117494 A1 | 3/2001 |
| WO | WO-0149285 A1 | 7/2001 |
| WO | WO-03094878 A1 | 11/2003 |
| WO | WO-2004056307 A2 | 7/2004 |
| WO | WO-2007132175 A2 | 11/2007 |
| WO | WO-2007133721 A2 | 11/2007 |
| WO | WO-2009045952 A1 | 4/2009 |

OTHER PUBLICATIONS

Ahlborg, et al., "Generation of Antibodies to Human IL-12 and Amphiregulin by immunization of Balb/c Mice with Diepitope Multiple Antigen Peptides," J. of Immunological Methods. 204(1):23-32 (1997).

Bakhos, "Gaussia Luciferase Reporter Assay for Monitoring of Biological Processes in Culture and in Vivo," Nature Protocols, 4(4):582-591 (2009).

Bals, et al., "The Peptide LL-37/hCAP-18 is Expressed in Epithelia of the Human Lung Where it Has Broad Antimicrobial Activity at the Airway Surface," Proc. Natl. Acad. Sci., 95(16):9541-9546 (1998).

BioGenic EGCG, May 20, 2009, [retieved May 20, 2009]. Retrieved from the Internet <URL: http://www.in-cosmetics.com/ExhibitorLibrary/826/EGCG-brochure-2.pdf.

Coffelt, et al., "Ovarian Cancers Overexpress the Antimicrobial Protein hCAP-18 and its Derivative LL-37 Increases Ovarian Cancer Cell Proliferation and Invasion," Int. J. Cancer, 22(5): 1030-1039 (2009).

Coffelt, et al., "The Pro-Inflamatory Peptide LL-37 Promotes Ovarian tumor Progression Through Recruitment of Multipotent Mesenchymal Stromal Cells," Proceedings of the National Academy of Sciences of the United States of America, 106(10):3806-3811 (2009).

(Continued)

*Primary Examiner* — Albert Navarro

(74) *Attorney, Agent, or Firm* — Foley Haug LLP

(57) ABSTRACT

The present invention relates to oral antibacterial compositions comprising trihydroxybenzoate derivatives, e.g., useful for the treatment of gum diseases (e.g., gingivitis or periodontitis) and to methods of using such compositions.

5 Claims, 7 Drawing Sheets

(56) References Cited

OTHER PUBLICATIONS

Coffelt., et al., "Supporting Information: The Pro-Inflamatory Peptide LL-37 Promotes Ovarian tumor Progression Through Recruitment of Multipotent Mesenchymal Stromal Cells," Proceedings of the National Academy of Sciences of the United States of America. 106(10):3806-3811 (2009).

Hosokawa, "Innate Immune Peptide LL-37 Displays Distinct Expression Pattern From Beta-Defensins in Inflamed Gingival Tissue," Clinical and Experimental Immunolgy, 146:218-225 (2006).

Midorikawa et al., "*Staphyloccus aureus* Suseptibility to Innate Antimicrobial Peptides, B-Defensins and CAP18, Expressed by Human Keratinocytes," Infection and Immunology. 71(7):3730-3739 (2003).

Ouhara et al., "Increased resistance to catiomic antimicrobial peptide LL-37 in methicillin-resistant strains of *Staphylococcus aureus*," Journal of Antimicrobial Chemotherapy, (2008).

Oya, et al., "Methylglyoxal Modification of Protein: Chemicals and Immunochemical Characterization of Methylglyoxal-Arginine Adducts," J. of Biol. Chem., 274(26):18492-18502 (1999).

Sakanaka, et al., "Antibacterial Substances in Japanes Green Tea Extract Against *Streptococcus mutans*, a Cariogenic Bacterium," Agric. Biol. Chem., 53(9):2307-2311 (1989).

Shamsi, et al., "Immunological Evidence for Methylglyoxal-Derived Modifications in Vivo. Determination of Antigenic Epitopes," J. of Biol. Chem., 273(12):6928-6936 (1998).

Shamsi, et al., "Methylglyoxal-Derived Modifications in Lens Aging and Cataract Formation," Investigative Opthalmology and Visual Science, 39(12):2355-2364 (1998).

Takeuchi, et al., "Immunological Detection of a Novel Advanced Glycation End-Product," Molecular Medicine; 7(11):783-791 (2001).

Toiletry Product Materials-BioGenic EGCG Powder, May 20, 2009, [retrieved May 20, 2009]. Retrieved from the Internet <URL: http://www.ecplaza.net/tradeleads/seller/5146242/toiletry-product-materialsbiogenic.html.

Uchida, et al., "Protein Modification by a Maillard Reaction Intermediate Methylglyoxal. Immunochemical Detection of fluorescent 5-Methylimidazolone derivatives in Vivo," FEBS Letters, 410(2-3):313-318 (1997).

Von Haussen, et al., "The host Defense Peptide LL-37/hCAP-18 is a Growth Factor for Lung Cancer Cells," Lung Cancer, 59(1):12-23 (2008).

Wan, et al., "Leukotriene B4 Triggers Release of the Cathelicidin LL-37 from Human Neutrophils: Novel Lipid-Peptide Interactions in Innate Immune Responses," The FASEB J., 21(11):2897-2905 (2007).

Fig.3 Suppression of DDX5 expression in OBA9 gingival epithelial cells using RNAi technology

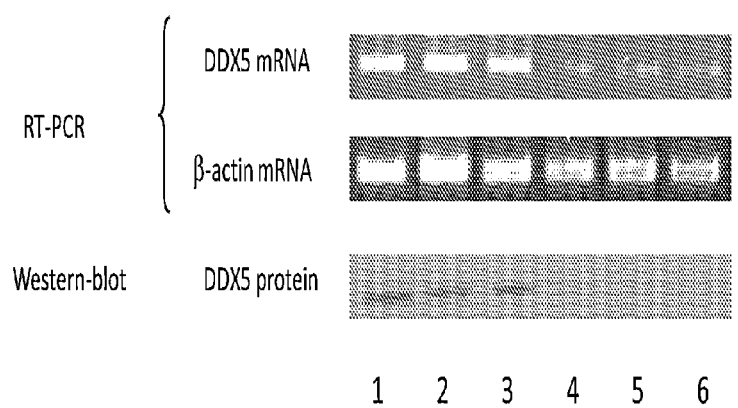

1 2 3 4 5 6

1 and 2; Control no siRNA
3; Control none target siRNA
4; DDX5 siRNA sequence A (5'; CCUGAUAGGCAAACUCUAAtt (SEQ ID NO: 2), UUAGAGUUUGCCUAUCAGGtc (SEQ ID NO: 3))
5; DDX5 siRNA sequence B (5'; GGCGAUGGGCCUAUUUGUUtt (SEQ ID NO: 4); 3' AACAAAUAGGCCCAUCGCCtc (SEQ ID NO: 5))
6; DDX5 siRNA sequence C (5', CCAAAAGAAGAUGUGAUGAtt (SEQ ID NO: 6); 3' UCAUCACAUCUUCUUUUGGtt (SEQ ID NO: 7))

ANTIBACTERIAL COMPOSITIONS

RELATED APPLICATIONS

This application is a Divisional Application of U.S. Ser. No. 12/762,234, filed on Apr. 16, 2010, which claims the benefit of U.S. Provisional Application No. 61/169,845 filed Apr. 16, 2009, entitled "Antibacterial Compositions" by Toshihisa Kawai, et al.

The entire teachings of the above application are incorporated herein by reference.

BACKGROUND

Gum disease is an example of a bacterial infection that affects a number of people. Gingivitis and periodontitis are common gum diseases that are problematic and, in certain instances, can be difficult to prevent or treat.

A need exists for an oral formulation that has anti-bacterial properties. In particular, a further need exists for oral formations that are effective in the prevention or treatment of gum disease and other bacterial infections.

SUMMARY OF THE INVENTION

The present invention relates to oral antibacterial compositions comprising trihydroxybenzoate derivatives, e.g., useful for the treatment of gum diseases (e.g., gingivitis or periodontitis) and to methods of using such compositions.

Surprisingly, we have found that an important pharmacophore in these compounds is trihydroxybenzoate. Compounds having trihydroxybenzoate moieties are effective primarily not by any direct antimicrobial action, but rather by potently stimulating the production of certain endogenous antimicrobial peptides, particularly LL-37 peptide, from epithelial cells. Trihydroxybenzoates stimulate LL-37 production by binding to the DEAD box polypeptide-S (DDX5).

The present invention relates provide oral care compositions for inhibiting oral bacteria, their uses and methods of treatment thereof, comprising trihydroxybenzoate derivatives. The current invention provides a method of stimulating the production of antimicrobial peptides in mammalian cells comprising contacting said cells with an effective amount of trihydroxybenzoate derivatives in free or salt form. The present invention further includes assessing a level of stimulation of the production of antimicrobial peptides; wherein an increase in the stimulation the production of antimicrobial peptides occurs, as compared to a control. Trihydroxybenzoate derivatives useful for the current invention include 3,4,5-trihydroxybenzoic acid (i.e., gallic acid), its isoform, 2,3,4-trihydroxybenzoic acid, $C_{1-4}$alkyl-3,4,5-trihydroxybenzoate (e.g., ethyl 3,4,5-trihydroxybenzoate), $C_{1-4}$alkyl-2,3,4-trihydroxybenzoate (e.g., ethyl 2,3,4-trihydroxybenzoate), EGCG and mixtures thereof, in free or salt form (Trihydroxybenzoate Derivatives of the Invention).

In particular, it is surprisingly found that Trihydroxybenzoate Derivatives of the present invention increases the production of endogenous antimicrobial peptides, particularly LL-37 in gingival and cheek mucosal epithelial cells, thereby efficiently suppresses bacterial (e.g., *Actinobacillus actinomycetemcomitans*) growth known to cause gum diseases. Significantly, trihydroxybenzoate derivatives of the present invention induce endogenous antibiotic peptide production without inducing the expression of host pro-inflammatory factors such as cytokines (e.g., TNFa, IL-1b and IL-6), eicosanoids (e.g., prostaglandin E2 and Leukotriene B4) that are known to elicit, augment and prolong inflammatory conditions.

Therefore, in a particular embodiment, the present invention provides an oral care composition (Composition 1) useful for inhibiting oral bacteria, comprising a polyphenol extract enriched with trihydroxybenzoate derivatives selected from one or more 3,4,5-trihydroxybenzoic acid, 2,3,4-trihydroxybenzoic acid, $C_{1-4}$alkyl 3,4,5-trihydroxybenzoate (e.g., ethyl 3,4,5-trihydroxybenzoate), $C_{1-4}$alkyl-2,3,4-trihydroxybenzoate (e.g., ethyl 2,3,4-trihydroxybenzoate), 3,4,5-trihydroxybenzoic acid, 2,3,4-trihydroxybenzoic acid, EGCG and mixtures thereof in free or salt form, e.g., enriched with at least 0.12 wt. %, preferably 0.12-10 wt. %, preferably 0.15-3 wt. %, more preferably 0.5-1.5 wt. %, most preferably 0.6 wt. % of trihydroxybenzoate derivatives. In a preferred embodiment, the extract is enriched with $C_{1-4}$alkyl 3,4,5-trihydroxybenzoate, $C_{1-4}$alkyl-2,3,4-trihydroxybenzoate or mixtures thereof. In yet another preferred embodiment, the extract is enriched with 2,3,4-hydroxybenzoic acid, 3,4,5-trihydroxybenzoic acid or mixtures thereof in free or salt form. In yet another preferred embodiment, the extract is enriched with EGCG.

Furthermore, it is also surprisingly found that Trihydroxybenzoate Derivatives of the Invention efficiently stimulate the production of antimicrobial peptides LL-37 in epithelial cells while dihydroxy catechins such as catechins and epicatechins show little or no induction of LL-37 expression in epithelial cells. Therefore, in another embodiment, the invention provides an oral care composition (Composition 2) comprising trihydroxybenzoate derivatives selected from one or more 3,4,5-trihydroxybenzoic acid, 2,3,4-trihydroxybenzoic acid, $C_{1-4}$alkyl 3,4,5-trihydroxybenzoate (e.g., ethyl 3,4,5-trihydroxybenzoate), $C_{1-4}$alkyl-2,3,4-trihydroxybenzoate (e.g., ethyl 2,3,4-trihydroxybenzoate), EGCG, catechin gallate and epicatechin gallate, and mixtures thereof in free or salt form, wherein said composition is substantially free of catechins having only a dihydroxybenzyl moiety, e.g., catechin and epicatechin, e.g., wherein the ratios of Trihydroxybenzoate Derivatives of the Invention to dihydroxy catechins is less than 10%, preferably less than 1%, more preferably less than 0.1%, more preferably less than 0.05%, even more preferably less than 0.01%, most preferably less than 0.001% of the amount of dihydroxy catechins generally found in tea extracts. In one preferred embodiment, Composition 2 comprises trihydroxybenzoate derivatives selected from 3,4,5-trihydroxybenzoic acid, 2,3,4-trihydroxybenzoic acid and mixtures thereof in free or salt form, wherein said composition is substantially free of catechin and epicatechin (other than catechin gallate and epicatechin gallate, which contain trihydroxybenzyl moiety). In another preferred embodiment, Composition 2 comprises trihydroxybenzoate derivatives selected from 2,3,4-trihydroxybenzoic acid, 3,4,5-trihydroxybenzoic acid and mixtures thereof in free or salt form, wherein said composition is substantially free of catechin and. In yet another preferred embodiment, Composition 2 comprises EGCG, wherein said composition is substantially free of catechin and epicatechins In yet another embodiment, the invention further provides an oral care composition (Composition 3) comprising trihydroxybenzoate derivatives selected from selected from 3,4,5-trihydroxybenzoic acid, 2,3,4-trihydroxybenzoic acid, $C_{1-4}$alkyl 3,4,5-trihydroxybenzoate (e.g., ethyl 3,4,5-trihydroxybenzoate), $C_{1-4}$alkyl 2,3,4-trihydroxybenzoate (e.g., ethyl 2,3,4-trihydroxybenzoate), EGCG or mixtures thereof in free or salt form, wherein said composition is substantially free of dihydroxy catechins and GCG, e.g., wherein the amounts of dihydroxy catechins and GCG is less than 10%, preferably less than 1%, more preferably less than 0.1%, more preferably less than 0.05%, even more preferably less than 0.01%, most preferably less than 0.001% of the amount of dihyroxy catechins and GCG generally found in tea extracts. In a specific embodiment, said dihydroxy catechins are catechins and epicatechins In yet another specific embodiment, the trihydroxybenzoate derivatives are selected from 3,4,5-trihydroxybenzoic acid, 2,3,4-trihydroxybenzoic acid and mixture thereof in free or salt form. In yet another specific embodiment, the trihydroxybenzoate derivatives are selected from $C_{1-4}$alkyl-3,4,5-trihydroxybenzoate (e.g., ethyl-3,4,5-trihydroxybenzoate), $C_{1-4}$alkyl-2,3,4-trihydroxybenzoate (e.g., ethyl 2,3,4-trihydroxybenzoate) and mixtures thereof. In yet another specific embodiment, the trihydroxybenzoate derivative is EGCG.

In still yet another embodiment, the invention provides an oral care composition (Composition 4) comprising trihydroxybenzoate derivatives selected from 3,4,5-trihydroxybenzoic acid, 2,3,4-trihydroxybenzoic acid, $C_{1-4}$alkyl 3,4,5-trihydroxybenzoate (e.g., ethyl 3,4,5-trihydroxybenzoate), $C_{1-4}$alkyl-2,3,4-trihydroxybenzoate (e.g., ethyl 2,3,4-trihydroxybenzoate), EGCG and mixtures thereof in free or salt form, wherein said composition is substantially free of other polyphenols (e.g., p-coumaric acid, caffeic acid, vanillic acid, ferulic acid, p-hydroxybenzoic acid, ellagic acid, anthocyanins, catechins, flavan-3-ols catechin, epicatechin, gallocatechin, epigallocatechin, epicatechin 3-O-gallate, catechin gallate, epicatechin gallate, quercetin, kaempferol, myricetin, fisetin, isoquercitrin, hyperoside, genistein, daidzei, lignins, proanthocyanidins, resveratrol and tannins), e.g., wherein these other polyphenols comprise less than 5 wt. % of the total composition, preferably less than 1%, more preferably less than 0.5 wt. %, even more preferably less than 0.05 wt. % and most preferably less than 0.01 wt. % of the total weight of the composition. In an embodiment, the composition of the present invention includes about 0.0001% to about 2% by weight of a Camellia extract, said extract comprises trihydroxybenzoate derivatives in a concentration from about 0.1 ug/ml to about 100 ug/ml; wherein the composition stimulate LL-37 production in gingival cells. The composition can further includes 0.001% to about 5% by weight of fluoride ion sources, water, abrasives, surfactants, foaming agents, vitamins, polymers, enzymes, humectants, thickeners, antimicrobial agents, preservatives, flavorings, colorings and a combinations thereof.

In yet another specific embodiment, the trihydroxybenzoate derivatives are selected from 3,4,5-trihydroxybenzoic acid, 2,3,4-trihydroxybenzoic acid and mixture thereof in free or salt form. In yet another specific embodiment, the trihydroxybenzoate derivatives are selected from $C_{1-4}$alkyl-3,4,5-trihydroxybenzoate (e.g., ethyl-3,4,5-trihydroxybenzoate), $C_{1-4}$alkyl 2,3,4-trihydroxybenzoate (e.g., ethyl 2,3,4-trihydroxybenzoate) and mixtures thereof. In yet another specific embodiment, the trihydroxybenzoate derivative is EGCG.

In a particular embodiment the invention provides a composition (Composition 5), comprises trihydroxybenzoate compounds, e.g., as described above for any of Compositions 1-4, wherein the trihydroxybenzoate compounds are shown to
  (i) Bind to or have an affinity for DDX5 and/or
  (ii) Stimulate LL-37 production.
For example, the invention provides a plant extract comprising trihydroxybenzoate compounds which extract is concentrated with compounds binding to DDX5, e.g., obtained using affinity purification, e.g., affinity chromatography or beads or other surface coated with DDX5 and/or a fragment or derivative of DDX5 capable of binding a trihydroxybenzoate compound. The invention likewise provides methods of making plant extracts comprising passing a solution over a surface coated with DDX5 and/or a fragment or derivative of DDX5 capable of binding a trihydroxybenzoate compound.

The oral composition may be in the form of a solid or semi-solid such as toothpaste, chewing gum or lozenges; or in a liquid such as a mouth rinse.

In another embodiment, the invention further provides Composition 1, 2, 3, 4 or 5, further comprises one or more of a fluoride ion source, water, abrasives, surfactants, foaming agents, vitamins, polymers, enzymes, humectants, thickeners, antimicrobial agents, preservatives, flavorings, colorings and/or combinations thereof.

In a particular embodiment, the invention provides Composition 1, 2, 3, 4 or 5 as follows:

5.1. Any of Composition 1-5, further comprising an abrasive.

5.2. Any of Composition 1-5, or 5.1, wherein the abrasive is selected from a calcium phosphate (e.g., dicalcium phosphate dihydrate), calcium sulfate, precipitated calcium carbonate, silica (e.g. hydrated silica), and combinations thereof.

5.3. Any of the preceding compositions comprising an abrasive in an amount of about 15 wt. % to about 70 wt. % of the total composition weight.

5.4. Any of the preceding compositions comprising a small particle abrasive having a d50 of <5 micrometers.

5.5. Any of the preceding compositions comprising at least one fluoride ion source.

5.6. Formula 5.5, wherein said fluoride ion source is selected from sodium fluoride, potassium fluoride and ammonium fluoride.

5.7. Formula 5.5 or 5.6, wherein said fluoride ion source provides from about 50-10,000 ppm, preferably, 100-1000 ppm, most preferably about 500 ppm.

5.8. Formula 5.5, 5.6 or 5.7, wherein said fluoride ion source is in the amount of about 0.15 wt. % to about 2.5 wt. % of the total composition weight.

5.9. Any of the preceding compositions comprising at least one surfactant.

5.10. Any of the preceding compositions comprising at least one surfactant selected from sodium lauryl sulfate, cocamidopropyl betaine, and combinations thereof.

5.11. Any of the preceding compositions comprising an anionic surfactant.

5.12. Any of the preceding compositions comprising sodium lauryl sulfate.

5.13. Any of the preceding compositions comprising at least one humectant.

5.14. Any of the preceding compositions comprising at least one humectant selected from glycerin, sorbitol and combinations thereof 5.15. Any of the preceding compositions comprising at least one polymer.

5.16. Any of the preceding compositions comprising at least one polymer selected from polyethylene glycols, polyvinylmethyl ether maleic acid copolymers, polysaccharides (e.g. cellulose derivatives, for example carboxymethyl cellulose, or polysaccharide gums, for example xanthan gum or carrageenan gum), and combinations thereof.

5.17. Any of the preceding compositions comprising gum strips or fragments.

5.18. Any of the preceding compositions comprising flavoring, fragrance and/or coloring.

5.19. Any of the preceding compositions comprising water.
5.20. Any of the preceding compositions comprising an antibacterial agent.
5.21. Any of the preceding compositions comprising an antibacterial agent selected from triclosan, herbal extracts and essential oils (e.g. rosemary extract, thymol, menthol, eucalyptol, methyl salicylate), bisguanide antiseptics (e.g., chlorhexidine, alexidine or octenidine), quaternary ammonium compounds (e.g., cetylpyridinium chloride), phenolic antiseptics, hexetidine, povidone iodine, delmopinol, salifluor, metal ions (e.g., zinc salts, for example, zinc citrate), sanguinarine, propolis and oxygenating agents (e.g., hydrogen peroxide, buffered sodium peroxyborate or peroxycarbonate).
5.22. Any of the preceding compositions comprising triclosan.
5.23. Any of the preceding compositions comprising an antibacterial agent in an amount of 0.01-5 wt. % of the total composition weight.
5.24. Any of the preceding compositions comprising triclosan in an amount of 0.01 to 1 wt. percent of the total composition weight.
5.25. Any of the preceding compositions comprising triclosan in an amount of about 0.3% of the total composition weight.
5.26. Any of the preceding compositions effective upon application to the oral cavity, e.g., with brushing, to improve oral health by:
  (i) reducing or inhibiting oral bacteria;
  (ii) preventing or treating gum diseases, oral malodor, and/or tooth decay;
  (iii) reducing or inhibiting pre-carious lesions of the enamel;
  (iv) reducing or inhibiting demineralization of the teeth;
  (v) reducing hypersensitivity of the teeth;
  (vi) reducing or inhibiting formation of dental caries;
  (vii) promoting healing of sores or cuts in the mouth;
  (viii) reducing levels of acid producing bacteria;
  (ix) increasing relative levels of antimicrobial LL-37 peptides in the oral cavity; and/or
  (x) reducing plaque accumulation.
5.27. A composition obtained or obtainable by combining the ingredients as set forth in any of the preceding compositions.
5.28. Any of the preceding compositions wherein the composition is in the form of toothpaste.
5.29. Any of the preceding compositions wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.
5.30. Any of Composition 1-5 or 5.1-5.27, wherein the composition is in the form of a mouthwash.
5.31. Any of Composition 1-5 or 5.1-5.27, wherein the composition is chewing gum.
5.32. Any of Composition 1-5 or 5.1-5.27, wherein said composition is in the form of a gel dentifrice.

As the invention uses a composition enriched with trihydroxybenzoate derivatives that is effective in stimulating LL-37 peptides, the compositions of the invention can optionally comprise other polyphenols, but in a smaller amount than normally would required in conventional oral care compositions for improving oral hygiene.

The invention thus further encompasses methods to improve oral health (Method 1) by (i) reducing or inhibiting oral bacteria, (ii) preventing or treating gum diseases (e.g., gingivitis or periodontitis) oral malodor, and/or tooth decay, (iii) reducing or inhibiting pre-carious lesions of the enamel, e.g., as detected by quantitative light-induced fluorescence (QLF) or electrical conductance measurement (ECM), (iv) reducing or inhibiting demineralization of the teeth, (v) reducing hypersensitivity of the teeth, (vi) reducing or inhibiting formation of dental caries, (vii) promoting healing of sores or cuts in the mouth, (viii) reducing levels of acid producing bacteria, (ix) increasing relative levels of antimicrobial LL-37 peptides, and/or (x) reducing plaque accumulation, comprising applying a Composition of the Invention, as described herein, e.g., Compositions 1-5 or any of 5.1-5.32, to the oral cavity, e.g., by applying a Composition of the Invention to the oral cavity of a mammal in need thereof.

Accordingly, the present invention pertains to methods of treating an individual having an oral cavity disease or condition by selecting an individual having an oral cavity disease or condition, wherein the oral cavity disease or condition involves a decreased level of antimicrobial peptide stimulation; and administering an amount of trihydroxybenzoate derivatives to the oral cavity; wherein the stimulation of the production of antimicrobial peptides occurs. Examples of oral cavity diseases or conditions includes thrush, gingivitis, periodontitis, oral candidiasis, salivary diseases associated with bacterial, viral, or fungal infections; Crohn's disease, irritable bowel syndrome, ulcerative colitis, *Helicobacter pylori* caused stomach ulcer, and gastrointestinal diseases associated with mucosal bacteria. The steps of the present invention allow for the stimulation of the production of antimicrobial peptide reduces one or more symptoms associated with the oral cavity disease or condition.

Similarly, the method of the present invention includes stimulating the production of antimicrobial peptides in cells of an individual, by selecting an individual having a decreased level of antimicrobial peptide stimulation, as compared to a level of antimicrobial peptide stimulation of a control; contacting said cells with an effective amount of one or more trihydroxybenzoate derivatives; wherein an increase in the stimulation of the production of antimicrobial peptides occurs, as compared to the decreased level of antimicrobial peptide stimulation prior to contacting the cells. The level of antimicrobial peptide stimulation can be assessed prior to contact the cells or after, or both. In an embodiment, the method includes assessing the level of LL-37 production.

It is known that dental plaque is a biofilm consists primarily of bacteria (e.g., *streptococcus mutans* and anaerobes) which deposits at the teeth. Plaque is the main etiological factor responsible for dental caries and periodontal diseases such as gingivitis, periodontitis, oral malodor, and/or tooth decay. By reducing or inhibiting oral bacteria in the dental cavity through the stimulation of the production of antimicrobial peptides such as LL-37 and hBD2 in gingival epithelial cells using the Compositions of the Invention, said compositions is effective in producing the conditions provided above in Method 1. Similarly, dental hypersensitivity and demineralization of teeth result when protective enamel is lost due to the acid by-product of the bacterial degradation of fermentable carbohydrate, these conditions may be ameliorated by increasing production of antimicrobial peptides in the gingival epithelial cells. Likewise, by increasing antimicrobial peptides, particularly peptide LL-3 in the gingival, thereby reducing pathogenic bacteria, the Compositions of the Invention are useful for promote healing of sores or cuts in the mouth.

The present invention includes methods for treating a bacterial infection in an individual by administering an amount of any composition described herein to the individual, wherein the bacterial infection is reduced. Examples of such bacterial infection include thrush, gingivitis, periodontitis, oral candidiasis, salivary diseases associated with bacterial, viral, or fungal infections; Crohn's disease, irritable bowel syndrome, ulcerative colitis, *Helicobacter pylori* caused stomach ulcer, and gastrointestinal diseases associated with mucosal bacteria.

In addition, the present invention is also useful for treating other bacterial conditions such as keratitis, conjunctivitis, keratoconjunctivitis and corneal blindness. Keratitis is a bacterial (e.g., *staphylococcus aureus*) infection of the cornea generally due to injury or from wearing contact lenses. Ocular LL-37 peptides possess potent antibacterial activity against Gram-Positive and Gram-negative bacteria most often responsible for bacterial keratitis as well as against the most common Gram-positive keratitis-producing organisms SE and SA. Moreover, LL-37 possess significant antiviral inhibitory activity against herpes simplex virus (HSV-1), which is the leading cause of corneal blindness. Similarly, LL-37 has demonstrated significant inhibitory activity in vitro against Ad 19, which is the major cause of conjunctivitis and epidemic keratoconjunctivitis. Therefore, by stimulating the production of LL-37, the Compositions of the Invention is useful for keratitis, conjunctivitis, keratoconjunctivitis and corneal blindness.

As mentioned above, the present invention provides a composition for and method of stimulating production of antimicrobial peptide LL-37 in epithelial cells without inducing pro-inflammatory factors such as cytokines (e.g., TNFa, IL-1b and IL-7) and eicosanoids (e.g., Prostagladin E2 and Leukotriene B4). As such, the Compositions of the invention are particularly useful for treating a bacterial infection wherein (a) the bacteria is antibiotic resistant, (b) the patient is allergic to antibiotics; (c) the patient is immuno-compromised (e.g., HIV/AIDS patients); or (d) the infection is of an oral cavity. Patients who are likely to benefit from the current invention include, for example, HIV/AIDS patients experiencing thrush.

Additionally, LL-37 is a potent antimicrobial against various staphylococcal species. However, the antibiotics currently available for staphylococcal infections are derived from synthetic compounds such that they can generate more virulent antibiotic-resistant strains of pathogenic bacteria, such as those found in Methicilin-resistant *Staphylococcus aureus* (MRSA). As trihydroxybenzoate derivatives of the current invention work by increasing the host's intrinsic peptide antibiotic production, such compositions may be used to treat MRSA, particularly in those patients who are immune-compromised as in HIV/AIDS patients or patients who have recently undergone transplant or are hypersensitive to traditional antibiotics used to treat these infections.

In another embodiment, the invention further provides a gene switch comprising a heterologous gene under control of an LL-37 promoter, stimulated by trihydroxybenzoate derivatives selected from 3,4,5-trihydroxybenzoic acid, 2,3,4-trihydroxybenzoic acid, c1-4-alkyl 3,4,5-trihydroxybenzoate (e.g., ethyl 3,4,5-trihydroxybenzoate), $C_{1-4}$alkyl 2,3,4-trihydroxybenzoate (e.g., ethyl 2,3,4-trihydroxybenzoate), EGCG, GCG and mixtures thereof in free or salt form.

In yet another embodiment, the present invention provides a screening method for measuring LL-37 expression, using trihydroxybenzoate derivatives as candidate or as positive control. In a further embodiment, said trihydroxybenzoate derivatives are selected from one or more 3,4,5-trihydroxybenzoic acid, 2,3,4-trihydroxybenzoic acid, $C_{1-4}$alkyl 3,4,5-trihydroxybenzoate (e.g., ethyl 3,4,5-trihydroxybenzoate), $C_{1-4}$alkyl 2,3,4-trihydroxybenzoate (e.g., ethyl-2,3,4-trihydroxybenzoate), EGCG, GCG and mixtures thereof in free or salt form.

In a further example, the present invention provides a method of screening for compounds useful as antimicrobial and anti-inflammatory compounds, e.g., by stimulating LL-37 expression, comprising measuring the binding of test compounds to DDX5. The present invention involves methods of obtaining a plant extract enriched for molecules that bind to DDX5 comprising contacting the material to be extracted to a surface coated with DDX5 or a fragment of derivative of DDX5 that binds a trihydroxybenzoate derivative.

Another embodiment of the present invention includes methods for screening for one or more compounds that stimulate the production of one or more antibacterial peptides by contacting the compound to be tested with the DDX5 polypeptide sufficiently to allow formation of a complex between the compound to be tested and the isolated polypeptide, to thereby form a complex; and assessing the presence, absence or amount of the complex; wherein the presence of the complex indicates that the compound stimulates production of one or more antibacterial peptides; and the absence of a complex indicates that the compound does not stimulate the production of one or more antibacterial peptides. The method can include, e.g., comparing the amount of the complex with to a control (e.g., wherein the control is the amount of LL-37-antibody complex obtained under the same conditions). The isolated polypeptide or compound to be tested can be detectably labeled. The method further includes, in an embodiment, contacting the complex with an antibody specific to said DDX5 or said complex. DDX5 or the antibody can be bound to a solid support.

The present invention relates to methods for assessing a compound for stimulation of an anti-microbial peptide in a sample by contacting the sample with a compound to be tested to allow stimulation of the anti-microbial peptide; contacting the sample with an antibody that binds to the anti-microbial peptide sufficient to allow formation of a complex between the sample and the antibody, to thereby form an antigen-antibody complex; and assessing the presence, absence or amount of the antigen-antibody complex; wherein the presence or an increased level of the anti-microbial peptide, as compared to a control, indicates that the compound stimulates production of the anti-microbial peptide, and the absence or decreased level of anti-microbial peptide, as compared to a control, indicates that the compound does not stimulate of the production of the anti-microbial peptide. Examples of antimicrobial peptides include LL-37, hBD2, hBD3, Ghrelin, Lysozyme or combination thereof. The method can also include comparing the amount of the antigen-antibody complex to a control. The antibody can be detectably labeled. The method further includes contacting the sample with a second antibody specific to the antigen or antigen-antibody complex. The anti-microbial peptide or the antibody can be bound to a solid support. In an embodiment, a trihydroxybenzoate derivative is used as a positive control.

The present invention further relates to methods for assessing a compound for stimulation of an anti-microbial peptide in a sample by contacting the sample with the compound to be tested sufficiently to allow stimulation of anti-microbial peptide; contacting the sample with at least two oligonucleotide primers in a polymerase chain reaction, wherein at least one of the oligonucleotide primers is specific for the nucleic acid sequence of anti-microbial peptide, sufficiently to allow amplification of the primers; and detecting in the sample the amplified nucleic acid sequence; wherein the presence the amplified nucleic acid sequence indicates that the compound stimulates production of the anti-microbial peptide, and the absence of the amplified nucleic acid sequence indicates that the compound does not stimulate of the production of the anti-microbial peptide. At least one of the oligonucleotide primers can include at least about 10 contiguous bases.

The present invention further embodies methods for assessing a compound for stimulation of an anti-microbial peptide in a sample by contacting the sample with the compound to be tested sufficiently to allow stimulation of the anti-microbial peptide; contacting the sample with one or more oligonucleotide probes specific for an isolated nucleic acid molecule of the anti-microbial peptide under high stringency conditions, sufficiently to allow hybridization between the sample and the probe; and detecting the nucleic acid molecule that hybridizes to the oligonucleotide probe in the sample; wherein the presence the hybridization indicates that the compound stimulates production of the anti-microbial peptide, and the absence of hybridization indicates that the compound does not stimulate of the production of the anti-microbial peptide

BRIEF DESCRIPTION OF THE DRAWINGS

FIG. 3 is a photograph of blots showing suppression of DDX5 (by RT-PCR: DDX5 mRNA, β-actin mRNA and by western blot: DDX5 protein using SEQ ID NOs: 2-7).

DETAILED DESCRIPTION OF THE INVENTION

Figure 1:
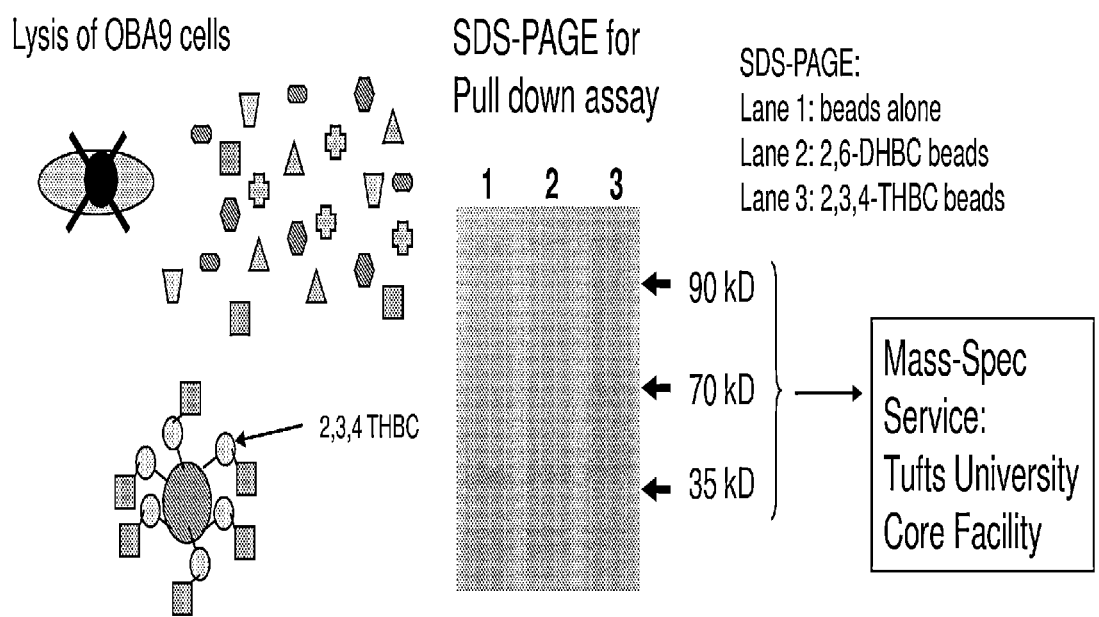
FIG. 1 is a schematic showing a pull down assay to determine counter ligand of benzoic acids expressed on OBA9 cells is DDX5. OBA9 cells were harvested and dissolved in lysis buffer. The resulting cell lysis solution was reacted with Sephadex beads conjugated with 2,6-dihydroxy benzoic acid (DHBC) and 2,3,4-trihydroxy benzoic acid (THBC). The cellular components pulled down with beads were separated in SDS-PAGE gel, and stained with Coomassie blue. The 35 kD and 70 kD bands specific to 2,3,4-THBC were subjected to Mass-Spec analysis at Tufts University Core Facility. The procedure for pull down assay includes preparation of cell lysate from gingival epithelial cell (OBA9) culture; preparation of beads conjugated with tri-hydroxy benzoic acid (THBC); incubation of beads with OBA9 cell lysate; remove unbound protein by washing beads; the proteins bound to beads are separated in SDS-PAGE; distinct bands to 2,3,4-THBC are sent for Mass-Spec service; and identification of molecular finger print of 2,3,4-THBC binding ligand.

"THBC" refers to chemical structures such as trihydroxybenzoates that comprise tri-hydroxy benzoic acid and its isoforms, which are found in the polyphenol extracts of natural plant products or in antioxidant food preservatives. THBC has been found to bind DEAD box polypeptide 5 (DDX5) expressed in the gingival epithelial cells. It was determined that 1) THBC present in epigallocatechin gallate (EGCG) binds to DDX5 present in the cytoplasm of gingival epithelial cells and 2) suppression of DDX5 expression in gingival epithelial cells using RNAi-specific to DDX5 mRNA resulted in inhibition of both mRNA and protein expression of LL-37 in the EGCG-stimulated gingival epithelial cells.

These findings prove that THBC acts directly on the molecule present in the cytoplasm of gingival epithelial cells. The finding that DDX5 is a ligand of EGCG in normal (non-cancer) cells demonstrates a novel biological mechanism elicited by EGCG.

THBC is thus useful for 1) oral health care products, 2) skin and mucosal health care products, 3) alternatives to, or supplements for, antimicrobial drugs, and 4) neutraceutical products.

The finding of EGCG-binding to DDX5 provides additional potential uses for THBC, including 1) DDX5 as a drug discovery target molecule and 2) detection of DDX5 in human and animal tissue samples as a diagnostic indicator of host innate immune potency.

In a further example, the invention provides a method of screening for compounds useful as antimicrobial and anti-inflammatory compounds, e.g., by stimulating LL-37 expression, comprising measuring the binding of test compounds to DDX5.

Using the anti-LL-37 antibodies, compounds that stimulate LL-37 and/or are mediated by DDX5 via the LL-37 pathway can be assessed using the assays described herein.

Most currently available oral and body health care products for treating and preventing inflammation rely on either direct action to host cells by anti-inflammatory drugs or on antibiotic action against microorganisms. THBC, however, utilizes a completely novel biological pathway. Specifically, THBC acts on host cells to increase the host body's production of antimicrobial peptides through its binding to DDX5. No agent is currently available that acts in a like manner to increase the host body's natural power to fight off microorganisms or to bind DDX5.

Moreover, most antibiotics currently used to prevent or treat infections are derived from synthetic compounds. As such, they can generate much more virulent antibiotic-resistant strains of pathogenic bacteria. For example, the emergence of antibiotic-resistant bacteria, such as Methicillin-resistant *Staphylococcus aureus* (MRSA), is one of the significant issues in medicine today. However, THBC, as noted above, is not a synthetic antibiotic. It actually increases the host body's intrinsic antibiotic peptide production. Thus, THBC is expected to be an important alternative where a diagnosis requires that an anti-infection regimen be antibiotic-free.

Compounds that can specifically bind DDX5 are considered to act in a manner similar to THBC, and are for example useful to an increase LL-37 expression in host cells. The signal-transduction molecules which convey signals elicited by THBC-activated DDX5 should also be involved in the up-regulation of LL-37 expression in host cells. In this case, the elucidation of such signal-transduction molecules downstream of DDX5 may establish another targets for drug discovery.

The biological action of THBC-binding of DDX5 to elicit LL-37 expression in host cells provides additional data about innate immunity, which is useful to investigators involved in basic medical and pharmacological research. Specifically, the cytoplasmic molecules currently known to elicit innate immune responses are nucleotide-binding oligomerization domain NOD and several other molecules. However, no studies have ever reported DDX5 as an innate immune response molecule. Therefore, the discovery of DDX5, as an innate immune regulatory molecule, enhances our understanding of the innate immune system and how to develop technologies dedicated to its manipulation.

THBC includes trihydroxybenzoate derivatives. As used herein, the term "trihydroxybenzoate derivatives" include 3,4,5-trihydroxybenzoic acid, 2,3,4-trihydroxybenzoic acid, $C_{1-4}$alkyl 3,4,5-trihydroxybenzoate (e.g., ethyl 3,4,5-trihydroxybenzoate), $C_{1-4}$alkyl 2,3,4-trihydroxybenzoate (e.g., ethyl 2,3,4-trihydroxybenzoate), EGCG, and mixtures thereof in free or salt form. In particular embodiments, for example, in methods for stimulating production of antimicrobial peptides, for treating keratitis, conjunctivitis, keratoconjunctivitis and corneal blindness, and for measuring LL-37 expression, the term trihydroxybenzoate derivatives further include GCG.

The term "dihydroxy catechins" herein refers to catchin and epicatechin, but does not include catechin galate and epicatechin gallate.

The term "polyphenols" herein refers to a large family of compounds commonly found in a wide variety of plants, fruits and vegetables. Polyphenols include, but not limited to (1) phenolic acid (e.g., p-coumaric, caffeic, vanillic, ferulic, p-hydroxybenzoic, gallic and ellagic acid) esters or glycosides conjugated with other natural compounds such as flavonoids, alcohols, hydroxyfatty acids, sterols, and glucosides; and (2) flavanoids which comprise of anthocyanins, catechins, flavan-3-ols catechin, epicatechin, gallocatechin, epigallocatechin, epicatechin 3-O-gallate, catechin gallate, epicatechin gallate, quercetin, kaempferol, myricetin, fisetin, isoquercitrin, hyperoside, genistein, daidzei, lignins, proanthocyanidins, resveratrol and tannins).

The phrase "substantially free of" as used herein refers to compositions wherein the ratio of Trihydroxybenzoate Derivatives of the Invention to, for example, dihydroxy catechins (e.g., catechin or epicatechin or GCG is less than 10%, preferably less than 1%, more preferably less than 0.1%, more preferably less than 0.05%, even more preferably less than 0.01%, most preferably less than 0.001% of the amount of dihyroxy catechins generally found in tea extracts, particularly green tea extract such as Oolong tea and green tea. It has been found that different kinds of tea extracts generally contain the following amounts of flavanols:

| Flavonols | Amounts (g) per 100 g of dry mass |
|---|---|
| EGCG | 0.93-5.74 |
| EGC | 0.73-3.25 |
| ECG | 0.17-1.16 |
| C | 0.04-0.48 |
| EC | 0.1-0.8 |
| Gallic acid | 0.06-0.62 |
| Theogallin | 0.17-0.97 |
| Caffeine | 2.25-4.33 |

Catechin and epicatechin therefore generally make up about 0.1-1.3% of tea extracts. Accordingly, a useful composition of the invention comprises trihydroxybenzoate derivatives and an amount of tea extract wherein said extract contains less than 0.14% of catechins and epicatechins. In a specific embodiment wherein the composition is substantially free of dihydroxybenzoate catechins and GCG, the composition contains, for example, less than 10%, preferably less than 1%, more preferably less than 0.1%, more preferably less than 0.05%, even more preferably less than 0.01%, most preferably less than 0.001% of the amount of dihyroxy catechins and GCG generally found in tea extracts. Wherein the composition is substantially free of other polyphenols (i.e., substantially free of polyphenols except for EGCG and gallic acid), said composition comprises trihydroxybenzoate derivatives and optionally polyphenols in an amount less than 5 wt. % of the total composition, preferably less than 1%, more preferably less than 0.5 wt. %, even more preferably less than 0.05 wt. % and most preferably less than 0.01 wt. % of the total weight of the composition.

The phrase "enriched with trihydroxybenzoate derivatives" herein refers to a composition wherein the total amounts of trihydroxybenzoate derivatives are at least 200% of the amount of gallic acid in polyphenol extracts, e.g., at least 0.12 wt. % of the total tea extract, preferably 0.12-10.00 wt. %, preferably 0.15-3.00 wt. %, more preferably 0.5-1.5 wt. %, most preferably 0.6 wt. %.

Fluoride Ion Source

Fluoride ion sources are well known for use in oral compositions as anti-caries agents and are preferably, but not necessarily contained in the Compositions of the Invention to provide the oral health benefits of the invention. Fluoride ions are contained in a number of oral care compositions for this purpose, particularly toothpastes. Patents disclosing such toothpastes include U.S. Pat. No. 3,538,230, Nov. 3, 1970 to Pader et al; U.S. Pat. No. 3,689,637, Sep. 5, 1972 to Pader; U.S. Pat. No. 3,711,604, Jan. 16, 1973 to Colodney et al; U.S. Pat. No. 3,911,104, Oct. 7, 1975 to Harrison; U.S. Pat. No. 3,935,306, Jan. 27, 1976 to Roberts et al; and U.S. Pat. No. 4,040,858, Aug. 9, 1977 to Wason, the contents of all of which are herein incorporated by reference.

Addition of fluoride ions to the Compositions of the Invention serves to protect teeth against decay. A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued Jul. 18, 1972, the contents of which are hereby incorporated by reference. Preferred fluoride ion sources for use herein include sodium fluoride, potassium fluoride and ammonium fluoride. Sodium fluoride is particularly preferred. Preferably the instant compositions provide from about 50-10,000 ppm, preferably, 100-1000 ppm, most preferably about 500 ppm of fluoride ions in the compositions that contact dental surfaces when used with the compositions of the present invention. Generally, the fluoride will be present at a level of from about 0.15% to about 2.5% by weight of the composition.

Abrasives

The Compositions of the Invention may include one or more abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasive polishing materials useful herein, as well as the other abrasives, generally have an average particle size ranging between about 0.1 and 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, abrasive materials useful in the practice of the oral care compositions in accordance with the invention include silica gels and precipitated amorphous silica having an oil absorption value of about less than 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns.

In particular embodiments, the abrasive materials comprise very small particles, e.g. having a d50<5 microns. For example, small particle silica (SPS) having a d50 of 3-4 microns, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3-8% SPS and about 25-45% of a conventional abrasive.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA® silica hydrogel composed of particles of colloidal silica having a water content of 29% by weight averaging about 7 to about 10 microns in diameter, and an oil absorption of less than about 70 ccc/100 g of silica is an example of a low oil absorption silica abrasive useful in the practice of the present invention. The abrasive is present in the oral care composition of the present invention at a concentration of about 10 to 60% by weight, in other embodiment about 20 to 45% by weight, and in another embodiment about 30 to 50% by weight.

Agents to Increase the Amount of Foaming

The oral care compositions of the invention also may include an agent to increase the amount of foam that is produced when the oral cavity is brushed.

Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Surfactants

Another agent optionally included in the oral care composition of the invention is a surfactant or a mixture of compatible surfactants. Suitable surfactants are those which are reasonably stable throughout a wide pH range, for example, anionic, cationic, nonionic or zwitterionic surfactants.

Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference.

In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetylpyridinium fluoride, and mixtures thereof.

Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which can be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

In a particular embodiment, the Composition of the Invention comprises an anionic surfactant, e.g., sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to 0.015% by weight.

Chelating Agents

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 1.0 wt. % pyrophosphate ions, about 1.5 wt. % to about 6 wt. %, about 3.5 wt. % to about 6 wt. % of such ions.

Polymers

The oral care compositions of the invention also optionally include one or more polymers, such as polyethylene glycols, polyvinylmethyl ether maleic acid copolymers, polysaccharides (e.g. cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g. potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Enzymes

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. No. 4,992,420; U.S. Pat. No. 4,355,022; U.S. Pat. No. 4,154,815; U.S. Pat. No. 4,058,595; U.S. Pat. No. 3,991,177; and U.S. Pat. No. 3,696,191 all incorporated herein by reference. An enzyme of a mixture of several compatible enzymes in the current invention constitutes about 0.002% to about 2.0% in one embodiment or about 0.05% to about 1.5% in another embodiment or in yet another embodiment about 0.1% to about 0.5%.

Water

Water may also be present in the oral compositions of the invention. Water, employed in the preparation of commercial oral compositions should be deionized and free of organic impurities. Water commonly makes up the balance of the compositions and includes about 10% to about 90%, about 20% to about 60% or about 10% to about 30% by weight of the oral compositions. This amount of water includes the free water which is added plus that amount which is introduced with other materials such as with sorbitol or any components of the invention.

Humectants

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Stimulation of Antimicrobial Peptides:

Human CAP-18, a human cathelicidin, was first identified in neutrophils and later shown to be expressed in various squamous epithelia, surface epithelial cells of the conducting airways, and serous and mucous cells of the submucosal glands, by keratinocytes in inflamed skin and by specific lymphocyte and monocyte populations. Human CAP-18 is the only human cathelicidin identified to date. It belongs to the cathelicidin family of antimicrobial peptides that are characterized by a conserved N-terminal cathelin domain and a variable C-terminal antimicrobial domain. This C-terminal domain can be cleaved off from the precursor by proteinases, releasing the active peptide. Exocytosed material from neutrophils contains hCAP-18 that has been proteolytically cleaved by proteinase-3 yielding the 4.5 kD active alpha helical peptide LL-37. LL-37 displays antimicrobial activity against a broad spectrum of microorganisms and possesses synergistic antibacterial effects with other antimicrobial peptides, such as defensins. It is believed that cathelicidins play a role in effective host defense against infection. A study has that mice deficient in the murine cathelicidin-related antimicrobial peptide suffer from more severe bacterial skin infections. Tjabring a, Sandra, et al., *J. Immunol,* 171:6690-6696 (2003). For another instance, deficiency in saliva LL-37 accords with occurrence of periodontal disease in patients with morbus Kostmann. Pütsep, Katrin, et al, Lancet, 360: 1144-1149 (2002).

As used herein hCAP-18 is considered to be the pro-form of LL-37. After cleavage by proteinases, a 4 kD polypeptide results as the active form of LL-37. As used herein, both forms are referred to as LL-37. The antibodies that bind to both forms of the LL-37, the pro-form and the active form are described in corresponding patent application Ser. No. 12/762,212 filed on even date herewith, entitled "New Methods of Making An Antibody and Compositions Thereof" by Toshihisa Kawai, et al., the entire teachings of which are incorporated herein by reference. LL-37 is one of the antimicrobial peptides used for the present invention. Examples of anti-microbial peptides include LL-37, hBD2, hBD3, Ghrelin, Lysozyme or a combination thereof.

It has been determined that LL-37, hBD2, hBD3, Ghrelin, Lysozyme has antimicrobial properties. For example, LL-37 is stimulated by certain compounds such as those having trihydroxybenzoate moieties. In particular, trihydroxybenzoate derivatives including 3,4,5-trihydroxybenzoic acid (i.e., gallic acid), its isoform, 2,3,4-trihydroxybenzoic acid, $C_{1-4}$alkyl 3,4,5-trihydroxybenzoate (e.g., ethyl 3,4,5-trihydroxybenzoate), $C_{1-4}$alkyl 2,3,4-trihydroxybenzoate (e.g., ethyl 2,3,4-trihydroxybenzoate), EGCG and mixtures thereof. In particular, "THBC" refers to chemical structures such as trihydroxybenzoates that comprise tri-hydroxy benzoic acid and its isoforms, which are found in the polyphenol extracts of natural plant products or in antioxidant food preservatives. As such trihydroxybenzoate moieties can be used as a positive control the LL-37, hBD2, hBD3, Ghrelin, Lysozyme assay described herein.

Compounds for stimulating production of anti-microbial peptides can be helpful in treating bacterial infection. Particularly, such compositions are particularly useful for treating a bacterial infection wherein (a) the bacteria is antibiotic resistant, (b) the patient is allergic to antibiotics; (c) the patient is immuno-compromised (e.g., HIV/AIDS patients); or (d) the infection is of an oral cavity. Additionally, LL-37, hBD2, hBD3, Ghrelin, Lysozyme are a potent antimicrobial against various staphylococcal species and particularly virulent antibiotic-resistant strains of pathogenic bacteria, such as those found in Methicilin-resistant *Staphylococcus aureus* (MRSA). Such compounds can also be useful for 1) oral health care products, 2) skin and mucosal health care products, 3) antimicrobial drugs, and 4) neutraceutical products.

Antibodies for Assessing Anti-Microbial Peptides:

Antibodies that are specific to LL-37, hBD2, hBD3, Ghrelin, Lysozyme or a combination thereof are helpful in determining compounds that stimulate antimicrobial peptide production, and would be helpful in treating the antibacterial disease or conditions. Compounds that stimulate antimicrobial peptide production can be included in compositions in which anti-microbial properties are needed. Since it is also reported that LL-37 can down regulate the production of pro-inflammatory cytokines, the increased production of LL-37 also results in the suppression of inflammatory responses. Scott M G, *J. Immunol.* 2002; 169:3883-389 (2002). Compounds that stimulate LL-37 hBD2, hBD3, Ghrelin, and/or Lysozyme can be included in health compositions (e.g., toothpaste, mouth wash, floss) and medications to treat various disease, including those related to the gut (e.g., for Crohn's disease or Colitis), and the like.

Antibodies can be used to assess the stimulation of antimicrobial peptide production. The term, "antibody," encompasses polyclonal antibodies, monoclonal antibodies, single chain antibodies, VHH antibodies, chimeric, humanized, primatized, CDR-grafted, and veneered antibodies. This term further includes portions derived from different species, human antibodies which are native or derived from combinatorial libraries, and the like. Conventional techniques can chemically join together the various portions of these antibodies. Genetic engineering techniques can also prepare the antibody as a contiguous protein. For example, nucleic acids encoding a chimeric or humanized chain can be expressed to produce a contiguous protein.

Specifically, the term "antibody fragment" refers to portion of an immunoglobulin having specificity to the LL-37 hBD2, hBD3, Ghrelin, Lysozyme or a portion thereof. The term, "antibody fragment", is intended to encompass fragments from both polyclonal and monoclonal antibodies including transgenically produced antibodies, single-chain antibodies (scFvs), recombinant Fabs, and recombinant camelid heavy-chain-only antibodies (VHHs). VHHs are also referred to as nanobodies.

Functional fragments of antibodies, including fragments of chimeric, humanized, primatized, veneered or single chain antibodies, can also be produced. Functional fragments or portions of the foregoing antibodies include those which are reactive with the LL-37, hBD2, hBD3, Ghrelin, Lysozyme. For example, antibody fragments capable of binding to LL-37, hBD2, hBD3, Ghrelin, Lysozyme or portion thereof, including, but not limited to scFvs, Fabs, VHHs, Fv, Fab, Fab' and F(ab')2 are encompassed by the invention. Such fragments can be produced by enzymatic cleavage or by recombinant techniques. For instance, papain or pepsin cleavage can generate Fab or F(ab')2 fragments, respectively. Antibodies can also be produced in a variety of truncated forms using antibody genes in which one or more stop codons has been introduced upstream of the natural stop site. For example, a chimeric gene encoding a F(ab')2 heavy chain portion can be designed to include DNA sequences encoding the CHI domain and hinge region of the heavy chain.

The term "antibody" also includes various forms of modified antibodies. For example, modification may occur by directly or indirectly attaching a detectable label. The detectable labels may include a radioisotope, spin label, antigen label such as a FLAG tag, enzyme label, fluorescent or chemiluminescent group and the like.

The term "sample" includes fluid and/or cells from an oral swab (e.g., containing saliva and/or epithelial cells from the oral cavity), tissue, fluid, whole blood, plasma, serum and aqueous blood components from a patient.

Methods of Assessment of Anti-Microbial Peptide Production and Methods of Making an Anti-Microbial Peptide Antibody:

Method for assessing the presence, absence or level of LL-37, hBD2, hBD3, Ghrelin, Lysozyme, in a sample, is encompassed by the present invention. Suitable assays include immunological methods, such as high throughput assays, radioimmunoassay, enzyme-linked immunosorbent assays (ELISA), chemiluminescence assays, and rapid immunochromatographic assays. A high throughput assays is a preferred embodiment of the present invention. Any method known now or developed later can be used for measuring LL-37, hBD2, hBD3, Ghrelin, or Lysozyme using the antibodies specific to these peptides.

In several of the preferred embodiments, immunological techniques detect the presence, absence, or levels of LL-37, hBD2, hBD3, Ghrelin, or Lysozyme described herein by means of an anti-LL-37, anti-hBD2, anti-hBD3, anti-Ghrelin, or anti-Lysozyme antibody (i.e., one or more antibodies). The term antibody includes one or more monoclonal antibodies or fragments thereof, and mixtures or cocktails thereof.

Anti-LL-37, anti-hBD2, anti-hBD3, anti-Ghrelin, or anti-Lysozyme antibody antibodies can be raised against appropriate immunogens, such as isolated and/or recombinant anti-microbial polypeptides described herein, analogs or portion thereof (including synthetic molecules, such as synthetic peptides).

To increase immunogenicity, the LL-37 protein underwent a chemical modification prior to being injected into an animal (e.g., mouse, rodent, rabbit, goat, monkey, camel, and the like) during the monoclonal antibody procedures. The chemical modification allows for a reaction with certain amino acids present in the protein. In this case, methylglyoxal was used to react with Arginine (R) and Lysine (K) present in LL-37. When methylglyoxal was combined with LL-37, the absorption by antigen presenting cells increased to thereby increase immunogenicity and develop a LL-37 specific antibody having a high affinity. Antigen presenting cells express the specific receptor (RAGE; the receptor for advanced glycation end products) for methylglyoxal-modified peptide and thereby allow for better absorption. Methylglyoxal is contacted with the antigen to be modified in an amount between about 1 nM and about 1 mM. This procedures can be applied to any of the anti-microbial peptides having between 1 and 30% total content of arginine, Lysine, or cysteine (C).

In one embodiment, antibodies are raised against an isolated, recombinant, active, chemically modified of LL-37, hBD2, hBD3, Ghrelin, or Lysozyme polypeptide described herein or portion thereof (e.g., a peptide) or against a host cell which expresses recombinant or chemically modified of LL-37, hBD2, hBD3, Ghrelin, or Lysozyme. In addition, cells expressing recombinant or modified antigenic of LL-37, hBD2, hBD3, Ghrelin, or Lysozyme polypeptides described herein, such as transfected cells, can be used as immunogens or in a screen for antibody which binds receptor.

Preparing the immunizing antigen can be done, as described above and any suitable technique, now known or later developed, can be used to produce polyclonal or monoclonal antibodies. The art contains a variety of these methods (see e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, fusing a suitable immortal or myeloma cell line, such as SP2/0, with antibody producing cells can produce a hybridoma. Animals immunized with the antigen of interest, after chemical modification, provide a cell that produces an antibody. Surprisingly, one or more antibodies specific for the native antigen are made and have a high binding affinity to the native antigen, even though the immunizing antigen was chemically modified. The immunized animal generally produces cells that make antibody that is specific to the antigen and these cells are typically cells from the spleen or lymph nodes. Cells from the spleen or lymph node are teased or separated from one another and cultured. Polyethylene glycol (PEG) or similar compound is used to fuse the myeloma cell line with the spleen or lymph node cells and a selective medium is used in which only fused cells can grow. Selective culture conditions isolate antibody producing hybridoma cells while limiting dilution techniques produce them. This mixture of cells is diluted and clones are grown from single parent cells generally in wells of a plate. The antibodies secreted by the different clones are then assayed for their ability to bind to the antigen. Researchers can use suitable assays such as ELISA to select antibody producing cells with the desired specificity. The hybridomas can be grown indefinitely in a suitable cell culture media, or they can be injected in mice into the peritoneal cavity, wherein they produce tumors containing an antibody-rich fluid called ascites fluid. The ascites that contains the antibody can be drained, bled or otherwise withdrawn from the animal. The antibody can be purified using standard purification techniques (e.g., ultra-filtration, dialysis, and chromatography).

Other suitable methods can produce or isolate antibodies of the requisite specificity. Examples of other methods include selecting recombinant antibody from a library or relying upon immunization of transgenic animals such as mice to make human monoclonal antibodies.

According to the method, an assay can determine the presence, absence or level of LL-37, hBD2, hBD3, Ghrelin, or Lysozyme peptides in a biological sample. Such an assay includes combining the sample to be tested with an antibody having specificity for LL-37, hBD2, hBD3, Ghrelin, or Lysozyme described herein, under conditions suitable for formation of a complex between antibody and LL-37, hBD2, hBD3, Ghrelin, or Lysozyme, and detecting or measuring (directly or indirectly) the formation of a complex. In the event that a compound is being assessed, the sample can be combined with the compound to be tested and incubated under conditions to allow for expression of LL-37, hBD2, hBD3, Ghrelin, or Lysozyme. The sample can be obtained directly or indirectly (e.g., provided by a healthcare provider), and can be prepared by a method suitable for the particular sample (e.g., saliva, epithelial cells from the oral cavity, urine, sputum, fecal matter, cerebral spinal fluid, whole blood, platelet rich plasma, platelet poor plasma, serum) and select an assay format. Methods of combining sample and antibody, and methods of detecting complex formation are also selected to be compatible with the assay format.

The assays described herein can be modified to assess the effect of a compound on LL-37, hBD2, hBD3, Ghrelin, or Lysozyme expression. In such a case, the compound can be introduced to the assay by contacting the compound with cells or samples that can express LL-37, hBD2, hBD3, Ghrelin, or Lysozyme. The cells or sample can be subjected to compound to be tested to determine if the compound has an effect on LL-37, hBD2, hBD3, Ghrelin, or Lysozyme expression. Alternatively, the subject, from whom the sample is taken, can be subjected to the compound and then a sample is taken. The sample can then be assessed for LL-37, hBD2, hBD3, Ghrelin, or Lysozyme expression, as described herein. Since it has been determined that trihydroxybenzoate stimulates LL-37, hBD2, hBD3, Ghrelin, or Lysozyme expression, a trihydroxybenzoate moiety can be used as a positive control in the assay.

Suitable labels can be detected directly, such as radioactive, fluorescent or chemiluminescent labels. They can also be indirectly detected using labels such as enzyme labels and other antigenic or specific binding partners like biotin. Examples of such labels include fluorescent labels such as fluorescein, rhodamine, chemiluminescent labels such as luciferase, radioisotope labels such as 32P, 125I, 131I, enzyme labels such as horseradish peroxidase, and alkaline phosphatase, galactosidase, biotin, avidin, spin labels and the like. The detection of antibodies in a complex can also be done immunologically with a second antibody, which is then detected (e.g., by means of a label). Conventional methods or other suitable methods can directly or indirectly label an antibody. Labeled primary and secondary antibodies can be obtained commercially or prepared using methods know to one of skill in the art (see Harlow, E. and D. Lane, 1988, Antibodies: A Laboratory Manual, (Cold Spring Harbor Laboratory: Cold Spring Harbor, N.Y.).

In a preferred embodiment, the presence, absence, or level of LL-37 in a sample is determined using a high throughput assay, an ELISA assay, a sandwich ELISA assay, or immunochromatographic assay.

For detection of LL-37, hBD2, hBD3, Ghrelin, or Lysozyme in a suitable sample, a sample (e.g., saliva) is collected. Samples can be processed as known in the art. The compound to be assessed can be contacted with the sample, or in contact with the subject prior to taking the sample. For example, the compound can be part of an oral composition that the subject uses.

In an embodiment, LL-37, hBD2, hBD3, Ghrelin, or Lysozyme is determined using an ELISA assay or a sandwich ELISA assay. In one embodiment, murine L2 is used as capture antibody and murine L7 is used as detector antibody.

In an embodiment, the assay further includes combining a suitable sample, and optionally the compound to be tested, with a composition having an anti-LL-37, anti-hBD2, anti-hBD3, anti-Ghrelin, or anti-Lysozyme polypeptide antibody as detector (e.g., biotinylated anti-microbial polypeptides MAb and HRP-streptavidin, or HRP-conjugated anti-microbial polypeptides Mab), and a solid support, such as a microtiter plate, having an anti-microbial polypeptide capture antibody bound (directly or indirectly) thereto. The detector antibody binds to a different anti-microbial polypeptide epitope from that recognized by the capture antibody, under conditions suitable for the formation of the complex. The assay then involves determining the formation of complex in the samples. The presence of or increase in LL-37, hBD2, hBD3, Ghrelin, or Lysozyme in a sample of an individual indicates the presence of a compound that increased expression or production of LL-37, hBD2, hBD3, Ghrelin, or Lysozyme, whereas the absence of or decrease in a LL-37, hBD2, hBD3, Ghrelin, or Lysozyme polypeptide indicates the compound to be tested that does not increase expression or production.

The solid support, such as a microtiter plate, dipstick, bead, pad, strip, or other suitable support, can be coated directly or indirectly with an anti-LL-37, anti-hBD2, anti-hBD3, anti-Ghrelin, or anti-Lysozyme polypeptide antibody or antimicrobial specific antigen. For example, an anti-LL-37, anti-hBD2, anti-hBD3, anti-Ghrelin, or anti-Lysozyme polypeptide antibody can coat a microtiter well, or a biotinylated anti-LL-37, anti-hBD2, anti-hBD3, anti-Ghrelin, or anti-Lysozyme polypeptide Mab can be added to a streptavidin coated support. With respect to a immunochromatographic assay, a pad or strip can be coated with an antibody specific for the antigen, and when a sample having the one or more of antigens described herein comes into contact with the antibody, the complex can turn a color with aid of a detector, as further described herein. A variety of immobilizing or coating methods as well as a number of solid supports can be used, and can be selected according to the desired format.

In another embodiment, the sample (or an LL-37, hBD2, hBD3, Ghrelin, or Lysozyme polypeptide standard) is combined with the solid support simultaneously with the detector antibody, and optionally with a one or more reagents by which detection is monitored. For example, the sample can be combined with the solid support simultaneously with (a) HRP-conjugated anti-LL-37 polypeptide Mab, or (b) a biotinylated anti-LL-37, hBD2, hBD3, Ghrelin, or Lysozyme polypeptide Mab and HRP-streptavidin.

A known amount of an LL-37, hBD2, hBD3, Ghrelin, or Lysozyme polypeptide standard can be prepared and processed as described above for a suitable sample. This LL-37, hBD2, hBD3, Ghrelin, or Lysozyme polypeptide standard assists in quantifying the amount of LL-37 detected by comparing the level of LL-37, hBD2, hBD3, Ghrelin, or Lysozyme in the sample relative to that in the standard. In one embodiment, active LL-37, hBD2, hBD3, Ghrelin, or Lysozyme is used as a standard.

A physician, technician, apparatus or a qualified person can compare the amount of detected complex with a suitable control to determine if the LL-37, hBD2, hBD3, Ghrelin, or Lysozyme levels are elevated or not. A control can be the level of LL-37, hBD2, hBD3, Ghrelin, or Lysozyme in a sample take from the subject, but not subjected to the compound to be tested. A positive control can be the level of LL-37, hBD2, hBD3, Ghrelin, or Lysozyme subjected to a known compound that stimulates LL-37, hBD2, hBD3, Ghrelin, or Lysozyme expression (e.g., trihydroxybenzoate moiety, or EGCG). A control can also be the average level of LL-37, hBD2, hBD3, Ghrelin, or Lysozyme for the particular sample, in a healthy population.

Typical assays for LL-37, hBD2, hBD3, Ghrelin, or Lysozyme are sequential assays in which a plate is coated with first antibody, sample is added, the plate is washed, second tagged antibody is added, and the plate is washed and bound second antibody is quantified. In another embodiment, a format in which antibodies and the sample are added simultaneously, in a competitive ELISA format, can achieve greater sensitivity.

A variety of methods can determine the amount of LL-37, hBD2, hBD3, Ghrelin, or Lysozyme in complexes. For example, when HRP is used as a label, a suitable substrate such as OPD can be added to produce color intensity directly proportional to the bound anti-LL-37, anti-hBD2, anti-hBD3, anti-Ghrelin, or anti-Lysozyme polypeptides mAb (assessed e.g., by optical density), and therefore to the LL-37, hBD2, hBD3, Ghrelin, or Lysozyme in the sample.

A technician, physician, qualified person or apparatus can compare the results to a suitable control such as a standard, or baseline levels of LL-37, hBD2, hBD3, Ghrelin, or Lysozyme in a sample from the same donor. For example, the assay can be performed using a known amount of LL-37, hBD2, hBD3, Ghrelin, or Lysozyme standard in lieu of a sample, and a standard curved established. One can relatively compare known amounts of the LL-37, hBD2, hBD3, Ghrelin, or Lysozyme standard to the amount of complex formed or detected.

The methods described herein for assaying compounds to determine antibacterial (e.g., antimicrobial) peptide stimulation, can also be used for assessing compounds for their ability to bind DDX5. See Exemplification. An antibody specific to DDX5 can be made and used in assays described herein. Compounds that stimulate the anti-microbial peptides bind to or have affinity to DDX5.

In an embodiment, methods for stimulating the production of antimicrobial peptides include contacting a mammalian cell with a trihydroxybenzoic acid derivative, and assessing the level of stimulation of the production of anti-microbial peptides. Samples of cells can be taken, as described herein, and contacted with a trihydroxybenzoate derivative in amounts described herein. The assessment of the level of antimicrobial peptides can be done using the assays and antibodies described herein.

Another embodiment of the invention includes stimulating the production of antimicrobial peptide in an individual. The method involves selecting an individual having a decreased level of antimicrobial peptide stimulation, as compared to a control. Samples from the individual can be taken, as described herein, and assayed to determine the level of antimicrobial peptide stimulation. The level can be compared to a prior level from the individual, or to a level from a healthy individual. In the event that the level is decreased, as compared to the control, as defined herein, then an amount of a compound that stimulates production of anti-microbial peptides can be administered. Various amounts and compositions are described here. The level can be re-assessed to determine if the level increase after administration.

Anti-LL-37, anti-hBD2, anti-hBD3, anti-Ghrelin, or anti-Lysozyme polypeptides mAb antibody can be produced recombinantly using a DNA sequence that encodes the antigen, which has been inserted into an expression vector and expressed in an appropriate host cell. DNA sequences encoding an anti-LL-37, anti-hBD2, anti-hBD3, anti-Ghrelin, or anti-Lysozyme antibody can, for example, be identified by assaying the antibody or fragment thereof against LL-37, hBD2, hBD3, Ghrelin, or Lysozyme and assessing binding and/or affinity characteristics.

The assays of the present invention include nucleic acid molecules (e.g., probes or primers) that hybridize to the anti-LL-37, anti-hBD2, anti-hBD3, anti-Ghrelin, or anti-Lysozyme antibody sequences, under high or moderate stringency conditions. In one aspect, the present invention includes molecules that are or hybridize to at least about 20 contiguous nucleotides or longer in length (e.g., 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000). Such molecules hybridize to one of anti-microbial peptides antibody nucleic acid sequences under high stringency conditions. The present invention includes such molecules and those that encode a polypeptide that has the functions or biological activity described herein.

Typically the nucleic acid probe comprises a nucleic acid sequence and is of sufficient length and complementarity to specifically hybridize to a nucleic acid sequence that encodes anti-LL-37 anti-hBD2, anti-hBD3, anti-Ghrelin, or anti-Lysozyme polypeptide. For example, a nucleic acid probe can be at least about 5%, 10%, 20%, 30%, 40%, 50%, 60%, 70%, 80% or 90% the length of the anti-LL-37, anti-hBD2, anti-hBD3, anti-Ghrelin, or anti-Lysozyme antibody nucleic acid sequence. The requirements of sufficient length and complementarity can be easily determined by one of skill in the art. Suitable hybridization conditions (e.g., high stringency conditions) are also described herein. Additionally, the present invention encompasses fragments of the polypeptides of the present invention or nucleic acid sequences that encodes a polypeptide wherein the polypeptide has the biologically activity of the anti-LL-37 polypeptides recited herein.

Stringency conditions for hybridization refers to conditions of temperature and buffer composition which permit hybridization of a first nucleic acid sequence to a second nucleic acid sequence, wherein the conditions determine the degree of identity between those sequences which hybridize to each other. Therefore, "high stringency conditions" are those conditions wherein only nucleic acid sequences which are very similar to each other will hybridize. The sequences can be less similar to each other if they hybridize under moderate stringency conditions. Still less similarity is needed for two sequences to hybridize under low stringency conditions. By varying the hybridization conditions from a stringency level at which no hybridization occurs, to a level at which hybridization is first observed, conditions can be determined at which a given sequence will hybridize to those sequences that are most similar to it. The precise conditions determining the stringency of a particular hybridization include not only the ionic strength, temperature, and the concentration of destabilizing agents such as formamide, but also factors such as the length of the nucleic acid sequences, their base composition, the percent of mismatched base pairs between the two sequences, and the frequency of occurrence of subsets of the sequences (e.g., small stretches of repeats) within other non-identical sequences. Washing is the step in which conditions are set so as to determine a minimum level of similarity between the sequences hybridizing with each other. Generally, from the lowest temperature at which only homologous hybridization occurs, a 1% mismatch between two sequences results in a 1° C. decrease in the melting temperature (Tm) for any chosen SSC concentration. Generally, a doubling of the concentration of SSC results in an increase in the Tm of about 17° C. Using these guidelines, the washing temperature can be determined empirically, depending on the level of mismatch sought. Hybridization and wash conditions are explained in Current Protocols in Molecular Biology (Ausubel, F. M. et al., eds., John Wiley & Sons, Inc., 1995, with supplemental updates) on pages 2.10.1 to 2.10.16, and 6.3.1 to 6.3.6.

High stringency conditions can employ hybridization at either (1) 1×SSC (10×SSC=3 M NaCl, 0.3 M $Na_3$-citrate.2H20 (88 g/liter), pH to 7.0 with 1 M HCl), 1% SDS (sodium dodecyl sulfate), 0.1-2 mg/ml denatured calf thymus DNA at 65° C., (2) 1×SSC, 50% formamide, 1% SDS, 0.1-2 mg/ml denatured calf thymus DNA at 42° C., (3) 1% bovine serum albumin (fraction V), 1 mM $Na_2$ ... EDTA, 0.5 M NaHP04 (pH 7.2) (1M NaHP04=134 g Na2HP04 ... 7H20, 4 ml 85% H3P04 per liter), 7% SDS, 0.1-2 mg/ml denatured calf thymus DNA at 65° C., (4) 50% formamide, 5×SSC, 0.02 M Tris-HCl (pH 7.6), IX Denhardt's solution (100X=10 g Ficoll 400, 10 g polyvinylpyrrolidone, 10 g bovine serum albumin (fraction V), water to 500 ml), 10% dextran sulfate, 1% SDS, 0.1-2 mg/ml denatured calf thymus DNA at 42° C., (5) 5×SSC, 5×Denhardt's solution, 1% SDS, 100 μg/ml denatured calf thymus DNA at 65° C., or (6) 5×SSC, 5×Denhardt's solution, 50% formamide, 1% SDS, 100 μg/ml denatured calf thymus DNA at 42° C., with high stringency washes of either (1) 0.3-0.1×SSC, 0.1% SDS at 65° C., or (2) 1 mM Na2EDTA, 40 mM NaHP04 (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated Tm of the hybrid, where Tm in ° C.=(2× the number of A and T bases)+(4× the number of G and C bases). For hybrids believed to be about 18 to about 49 base pairs in length, the Tm in ° C.=(81.5° C.+16.6(log 10M)+0.41(% G+C)−0.61 (% formamide)−500/L), where "M" is the molarity of monovalent cations (e.g., Na+), and "L" is the length of the hybrid in base pairs.

Methods of Treatment:

The present invention relates to methods for treating oral cavity diseases or conditions in individuals by administering an amount of an anti-microbial peptide stimulation compound. The present invention also relates to methods for treating bacterial infections in an individual. In particular, the present invention relates to treating and/or preventing diseases in an individual by anti-microbial peptide stimulation compound administration. To treat an individual with an oral/bacterial disease or condition means to alleviate, ameliorate or reduce the severity of one or more of symptoms associated with the oral/bacterial disease or condition. Prevention of a disease or condition refers to delaying or suppressing the onset of the one or more symptoms of the disease or condition. Additionally, the present invention encompasses reducing the severity of one or more symptoms associated with the oral/bacterial disease or condition, which refers to minimizing the extent of one or more such symptoms that are experienced by the individual.

Diseases or conditions, including oral disease or conditions, included in the methods of the present invention are those that are caused by bacterial infection. Such diseases are known in the art and include e.g., thrush, gingivitis, periodontitis, oral candidiasis, salivary diseases associated with bacterial, viral, or fungal infections; Crohn's disease, irritable bowel syndrome, ulcerative colitis, *Helicobacter pylori* caused stomach ulcer, and gastrointestinal diseases associated with mucosal bacteria. Additional examples of such infections include Methicillin-resistant *staphylococcus aureus* (MRSA), pneumonia, meningitis, urinary tract infections, sinusitis, gastritis and the like.

Methods for determining if an individual has such a disease include diagnostic tests and evaluations that are known in the art. Bacterial diseases or infections can be determined by taking a sample from the individual and culturing the sample to determine if the bacterial grows.

Modes and Manner of Administration, Dosages

Compounds that stimulate anti-microbial peptide production are administered for use with the methods described herein. Examples of such compounds include trihydroxybenzoate derivatives, as described in detail herein.

Such compounds used in the present invention can be administered with or without a carrier. The terms "pharmaceutically acceptable carrier" or a "carrier" refer to any generally acceptable excipient or drug delivery composition that is relatively inert and non-toxic. Exemplary carriers include sterile water, salt solutions (such as Ringer's solution), alcohols, gelatin, talc, viscous paraffin, fatty acid esters, hydroxymethylcellulose, polyvinyl pyrolidone, calcium carbonate, carbohydrates (such as lactose, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.). Such preparations can be sterilized and, if desired, mixed with auxiliary agents, e.g., lubricants, preservatives, stabilizers, wetting agents, emulsifiers, salts for influencing osmotic pressure, buffers, coloring, preservatives and/or aromatic substances and the like which do not deleteriously react with the active compounds. Typical preservatives can include; potassium sorbate, sodium metabisulfite, methylparaben, propyl paraben, thimerosal, chloral derivative, etc. A carrier (e.g., a pharmaceutically acceptable carrier) is preferred, but not necessary to administer the compound.

The anti-microbial peptide stimulation compound can be a liquid solution, suspension, emulsion, tablet, pill, capsule, sustained release formulation, or powder. The method of administration can dictate how the composition will be formulated. For example, the composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

The anti-microbial peptide stimulation compound used in the invention can be administered intravenously, parenterally, intramuscular, subcutaneously, orally (e.g., Cenestin, Estinyl, Estrace, Menest, Ogen, Premarin), nasally, topically (e.g., Estrace, Ogen, Ortho Dienestrol, Premarin), by inhalation, by implant (temporarily, e.g., Estring, Femring), by injection, by suppository (Vagifem) or transdermally (e.g., Alora, Climara, Esclim, Estraderm, Vivelle, Vivelle-Dot). The composition can be administered in a single dose or in more than one dose over a period of time to confer the desired effect (e.g., periodically, daily, weekly, monthly, yearly, etc.). In one embodiment, anti-microbial peptide stimulation compound, in particular to be administered has about 0.0001% to about 2% by weight of a Camellia extract, and the extract includes trihydroxybenzoate derivatives in a concentration from about 0.1 ug/ml to about 100 ug/ml.

The actual effective amounts of compound or drug can vary according to the specific composition being utilized, the mode of administration and the age, weight and condition of the patient. For example, as used herein, an effective amount of the drug is an amount which stimulates anti-microbial peptide production. Dosages for a particular individual patient can be determined by one of ordinary skill in the art using conventional considerations, (e.g. by means of an appropriate, conventional pharmacological protocol).

For enteral or mucosal application (including via oral and nasal mucosa), particularly suitable are tablets, liquids, drops, suppositories or capsules. A syrup, elixir or the like can be used wherein a sweetened vehicle is employed. Liposomes, microspheres, and microcapsules are available and can be used.

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

EXAMPLES

The following examples illustrate an oral composition of the described invention as compared to other formulations of similar compositions. Unless otherwise specified, all percentages are by weight.

Example 1

Induction of LL-37 Peptides

Induction of LL-37 and hBD2 mRNA Expression in Human Gingival Epithelial Cells.

Both LL-37 and hBD2 mRNA expression in OBA9 cells are induced after a 4-hour exposure to green tea polyphenol extract, Teaflan 90S (EGCG 50%, ECG 13%), and purified EGCG (95% pure, SIGMA) at concentrations of 0.1, 1.0 and 10 ug/ml. EGCG increases the production of LL-37 and hBD2 at the mRNA level in the human gingival epithelial cell line OBA9 (FIG. 1) as well as the human lung carcinoma cell line A549.

In Vitro Induction of LL-37 Protein Expression in Human Gingival Epithelial Cells.

Using ELISA systems to detect LL-37 (Forsyth in-house) and hBD2 (Peprotech), 33 natural compounds (20 ug/ml) are examined for their ability to induce LL-37 and hBD2 from OBA9 cells. Although the sensitivity of the hBD2 ELISA is higher than that of LL-37 ELISA (10 pg/ml vs 1 ng/ml, respectively), the induction of LL-37 is more prominent than hBD2 (FIG. 2 A&B, LL-37; C&D, hBD2). Trihydroxybenzoate derivatives and control mitogenic agents, PMA and Poly IC, induced LL-37, whereas trihydroxybenzoate derivatives, PMA and Poly IC have minimal induction activities. Bactericidal effects of LL-37 and hBD2 are, in general, potent. Therefore, although hBD2 induction was significantly elevated compared to the non-stimulated control, the concentration of expressed hBD2 appeared insufficient to kill bacteria.

The trihydroxybenzoate derivatives of the Invention and rosemarinic acid, courmarin, catechin gallate, epicatechin gallate, epigallocatechin, and tannic acid are tested to induce LL-37 from OBA9 cells in the absence of EGCG. Rosemarinic acid and courmarin, which lack 3,4,5-trihydroxy benzoate, showed little or no induction of LL-37 expression by OBA9 cells. Therefore, gallic acid appears to be more potent than 3,4,-dihydroxy benzoate in the induction of LL-37 expression by cultured gingival epithelial cells.

Culture Supernatant of EGCG-Treated Human Gingival Epithelial Cells.

The culture supernatant isolate from OBA9 is treated with 1) EGCG, 2) catechin, 3) 2,4-dihydroxy benzoic acid, and 4) 3,4,5-tri-hydroxy benzoic acid (20 ug/ml, respectively) and examined for their bactericidal effects on *Actinobacillus* actinomycetemcomitans Y4 (Aa Y4). The culture supernatant of EGCG- and 3,4,5-tri-hydroxy benzoic acid-treated OBA9 cells show more bactericidal effects than control non-treated OBA9 supernatant or supernatant of OBA9 treated with catechin or with 2,4-dihydroxy benzoic acid. Therefore, 3,4,5-tri-hydroxy benzoic acid and EGCG which contains gallic acid both appear to have higher antimicrobial effects than the compounds which do not have the structural isomers of gallic acid In Vivo Induction of LL-37 mRNA and Protein Expression by Human Cheek Epithelial Cells.

Cheek epithelium is utilized for monitoring LL-37 mRNA and protein expression to determine if Trihydroxybenzoate Derivatives of the Invention can induce LL-37 in vivo. Total RNA is extracted from cheek epithelial cells after application of mouthwash with EGCG (40 ug/ml), and LL-37 mRNA expression by the cheek epithelial cells is determined by RT-PCR. mRNA for LL-37 is up-regulated after only 5 minutes from application of the mouthwash with EGCG, whereas the internal control b-actin is expressed constitutively. The isolated cheek cells are also subjected to Western blot analysis for protein expression of LL-37 by cheek epithelium using anti-LL-37 monoclonal antibody. The expression of both the proform (18 kD, also termed as hCAP18) and secreted form (4.5 kD) of LL-37 (12) in cheek epithelial cells is induced by Trihydroxybenzoate Derivatives of the Invention (e.g., EGCG (95% SIGMA), or by EGCG (90% Teavigo)). The immunohistochemical analysis for LL-37 expression stained with anti-LL-37 monoclonal antibody also demonstrate the increased expression of LL-37 in the cheek epithelial cells after ex vivo stimulation.

Tri-Hydroxy Benzoic Acid.

In order to investigate the structure-function relationship underlying EGCG-mediated induction of LL-37 from human gingival epithelial cell line OBA9, different isomers of benzoic acids are examined for their effects on the LL-37 expression by OBA9 cells. Each isomer of benzoic acids is coupled to NBS-activated Sepharose gel (Pierce) using a cross-linker, 1-Ethyl-3-[3-dimethylaminopropyl]carbodiimide (EDC, Pierce). The isomers of benzoic acids include 1) 2,6-di-hydroxy benzoic acid, 2) 2,3,4-tri-hydroxy benzoic acids, 3) 3,4,5-tri-hydroxy benzoic acids, and 4) 2,4,6-tri-hydroxy benzoic acids. Only 2,3,4-tri-hydroxy benzoic acids and 3,4,5-tri-hydroxy benzoic acids, but not 2,6-di-hydroxy benzoic acids or 2,4,6-tri-hydroxy benzoic acids, show the induction of LL-37 expression by OBA9 cells.

Example 2

Binding to DDX5

Figure 2:
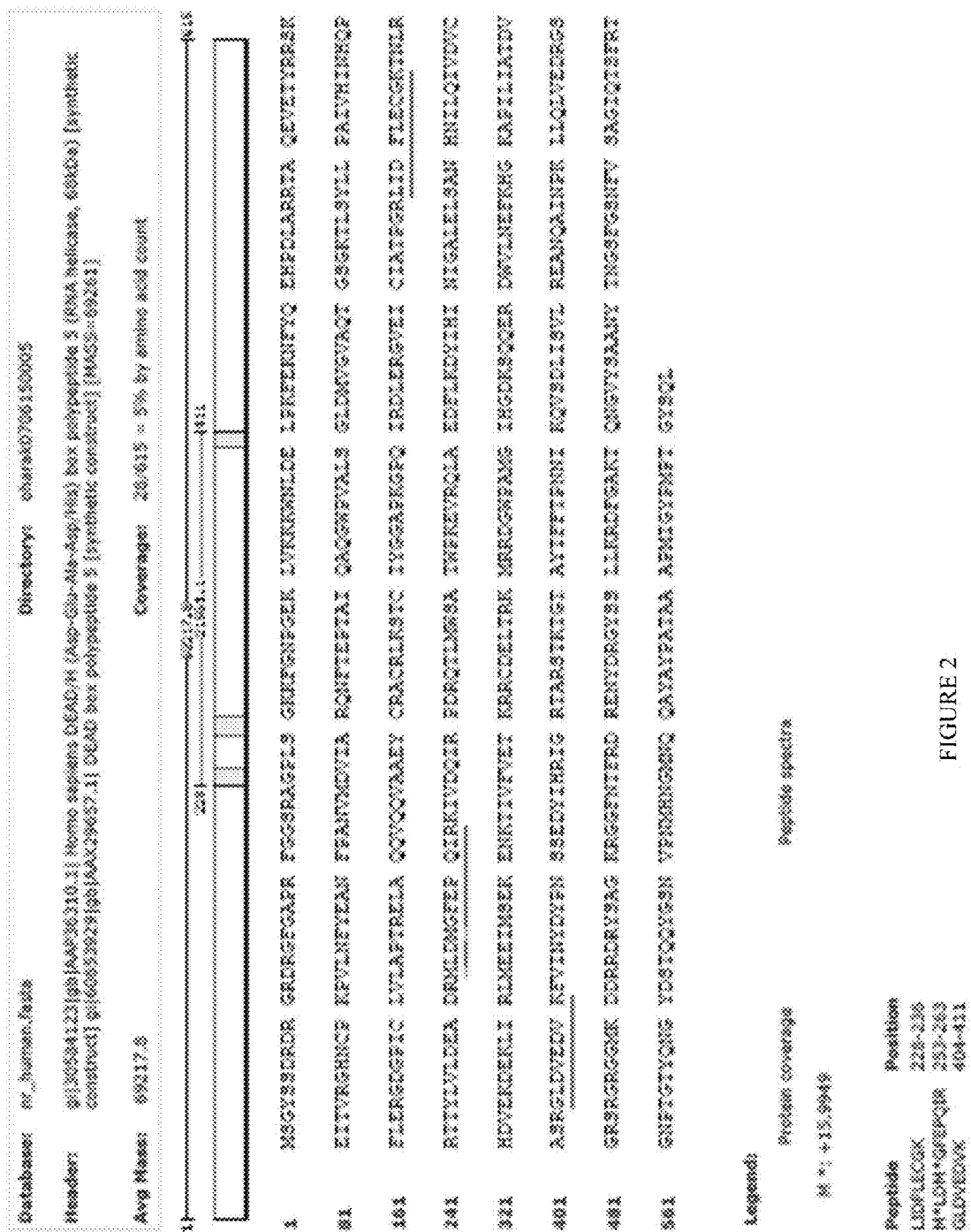
FIG. 2 is a schematic including the molecular finger print found in 70 kD band specific to 2,3,4-THDC that is DDX5 (SEQ ID NO: 1). The 35 kD, 70 kD and 90 kD bands specific to 2,3,4-THBC were subjected to Mass-Spec analysis service. While 35 kD and 90 kD bands did not contain any distinct protein(s) to 2,3,4-THDC beads, 70 kD band contain DEAD box polypeptide 5 (DDX5), which was only found in 2,3,4-THDC beads. Result data sheet that identified DDX5 in 70 kD band is shown.

In order to confirm if LL-37 induction in epithelial cells by EGCG is dependent on the activation of cell ligand (either cytoplasm or cell surface), or previously known anti-oxidant effects by EGCG, 3,4,5-tri-hydroxy benzoic acid-coupled beads and control 2,6-di-hydroxy benzoic acid-coupled beads are utilized to pull down the possible ligand for 3,4,5-tri-hydroxy benzoic acid. After incubation of each bead with cell lysate of OBA9, the beads are washed, and the cellular materials that bind to the beads are separated in SDS-PAGE. At least 3 bands (MW 35 kD, 70 kD and 90 kD), which are distinct to 3,4,5-tri-hydroxy benzoic acid, are detected, as compared to the other beads (control, 2,6-di-hydroxy benzoic acid and control plain beads). The 3 bands (35 kD, 70 kD and 90 kD) are cut out from SDS-PAGE gel and submitted for Mass-Spectrometry analysis service at Tufts University Core Facility. While the 35 kD and 90 kD bands do not contain any distinct protein to 3,4,5-tri-hydroxy benzoic acid, the 70 kD band appears to contain DEAD box polypeptide 5 (DDX5) (FIG. 2). This result indicates that 3,4,5-tri-hydroxy benzoic acid binds to DDX5 expressed in gingival epithelial cells with high affinity, and provides strong evidence that THBC-mediated LL-37 expression in epithelial cells does result from the ligation of DDX5 by THBC present in EGCG.

Direct targeting of DDX5 by synthetic chemicals different from THBC, or by protein agonists, should result in the development of additional forms of regimens that increase the LL-37 expression by epithelial cells.

Our hypothesis that THBC induction of LL-37 expression is mediated via binding to DDX5 is further supported by the finding that inhibition of DDX5 expression in gingival epithelial cells (OBA9) reduces EGCG-mediated LL-37 expression. Confluent OBA9 cells in a tissue culture plate are treated with or without DDX5-specific siRNA sequences (three different siRNA sequences specific to DDX5 are examined). After 24 h and 48 h incubation, total RNA and proteins are extracted, respectively, from the OBA9 cells. The results of RT-PCR for DDX5 mRNA and internal control of β-actin mRNA and the results of Western blot for DDX5 protein demonstrate that all three different DDX5 siRNA sequences remarkably suppress the expression of DDX5 at both mRNA and protein levels. The OBA9 cells pre-incubated with non-target siRNA and DDX5-siRNA for 48 hours are restimulated with EGCG (40 ng/ml) for 30 min, and mRNA expression for LL-37 and 13-actin was detected by RT-PCR. Very importantly, LL-37 expression induced in OBA9 cells by EGCG stimulation is remarkably suppressed by pretreatment of OBA9 cells with DDX5-siRNA. Effects of DDX5-siRNA treatment on EGCG-mediated LL-37 protein expression by OBA9 cells is measured by ELISA. The EGCG-mediated induction of LL-37 production is detected as early as 30 min until 24 hours after EGCG stimulation in the OBA9 cells which do not receive pretreatment (medium alone) or which are treated with control non-target siRNA sequence. However, inhibition of DDX5 expression using DDX5-siRNA in OBA9 cells significantly suppresses the EGCG-mediated LL-37 production by OBA9 cells for all incubation periods examined (from 30 min to 24 h). These results indicate that ligation of DDX5 with 3,4,5-THBC present in EGCG can induce LL-37 expression from gingival epithelial cells.

Example 3

Formulations

In one embodiment, the composition of the invention may be prepared using the following ingredients:

TABLE 1

| MATERIAL | WEIGHT % |
| --- | --- |
| Polyphenol extract-1 | 0.200 |
| Trihydroxybenzoate derivatives | 0.050 |
| Carboxymethyl cellulose | 1.100 |
| Sodium Saccharin | 0.200 |
| Sodium Monofluorophosphate | 1.100 |
| Tetrasodium pyrophosphate | 0.500 |
| Phosphoric acid 85% | 0.600 |
| Dicalcium phosphate dihydrate | 46.500 |
| Sodium lauryl sulfate 35% | 4.071 |
| Flavor | 0.950 |
| Glycerin | 22.000 |
| Deionized Water | Balance |
| TOTAL | 100.000 | wherein polyphenol extract-1 comprises between 0.06-0.6% gallic acid.

In another embodiment, the composition of the invention may be prepared using the following ingredients:

TABLE 1

| MATERIAL | WEIGHT % |
| --- | --- |
| Polyphenol extract-2 | 0.200 |
| Trihydroxybenzoate derivatives | 0.050 |
| Carboxymethyl cellulose | 1.100 |
| Sodium Saccharin | 0.200 |
| Sodium Monofluorophosphate | 1.100 |
| Tetrasodium pyrophosphate | 0.500 |
| Phosphoric acid 85% | 0.600 |
| Dicalcium phosphate dihydrate | 46.500 |
| Sodium lauryl sulfate 35% | 4.071 |
| Flavor | 0.950 |
| Glycerin | 22.000 |
| Deionized Water | Balance |
| TOTAL | 100.000 | wherein polyphenol extract-2 comprises less than 0.04% of catechins and epicatechins. In yet another embodiment, the composition of the invention comprises the ingredients disclosed in Table 3, wherein polyphenol extract-2 contains less than less than 0.04% of catechins and epicatechins and less than 0.005% of GCG (Polyphenol extract-3).

In a certain embodiment, the compositions of the invention is as follows:

| Toothpaste-Formulation A | |
| --- | --- |
| MATERIAL | WEIGHT % |
| Polyphenol extract-1 | 0.200 |
| Trihydroxybenzoate derivatives | 0.050 |
| Dibasic calcium phosphate | 42.000 |
| Glycerine | 18.000 |
| Sodium lauryl sulfate | 1.200 |
| Saccharin sodium | 0.090 |
| Flavoring agent | 1.000 |
| Water | Balance |
| TOTAL | 100.000 |

| Toothpaste-Formulation B | |
| --- | --- |
| MATERIAL | WEIGHT % |
| Polyphenol extract-2 or extract-3 | 0.200 |
| Trihydroxybenzoate derivatives | 0.050 |

Toothpaste-Formulation B

| MATERIAL | WEIGHT % |
| --- | --- |
| Dibasic calcium phosphate | 42.000 |
| Glycerine | 18.000 |
| Sodium lauryl sulfate | 1.200 |
| Saccharin sodium | 0.090 |
| Flavoring agent | 1.000 |
| Water | Balance |
| TOTAL | 100.000 |

Toothpaste-Formulation C

| MATERIAL | WEIGHT % |
| --- | --- |
| Polyphenol extract | 0.001 |
| Trihydroxybenzoate derivatives | 0.250 |
| Dibasic calcium phosphate | 42.000 |
| Glycerine | 18.000 |
| Sodium lauryl sulfate | 1.200 |
| Saccharin sodium | 0.090 |
| Flavoring agent | 1.000 |
| Water | Balance |
| TOTAL | 100.000 |

Toothpaste-Formulation D

| MATERIAL | WEIGHT % |
| --- | --- |
| Polyphenol extract-I | 0.100 |
| Trihydroxybenzoate derivatives | 0.050 |
| Dibasic calcium phosphate | 42.000 |
| Glycerine | 18.000 |
| Sodium lauryl sulfate | 1.200 |
| Saccharin sodium | 0.090 |
| Flavoring agent | 1.000 |
| Water | Balance |
| TOTAL | 100.000 |

Mouth wash-Formulation A

| MATERIAL | WEIGHT % |
| --- | --- |
| Polyphenol extract-I | 0.200 |
| Trihydroxybenzoate derivatives | 0.050 |
| Sodium lauryl sulfate | 0.800 |
| Glycerine | 7.000 |
| Sorbitol | 5.000 |
| Ethyl alcohol | 15.000 |
| !-Menthol | 0.050 |
| Flavoring agent | 0.040 |
| Saccharin sodium | 0.100 |
| Water | Balance |
| TOTAL | 100.000 |

Mouth wash-Formulation B

| MATERIAL | WEIGHT % |
| --- | --- |
| Polyphenol extract-2 or extract-3 | 0.200 |
| Trihydroxybenzoate derivatives | 0.050 |
| Sodium lauryl sulfate | 0.800 |
| Glycerine | 7.000 |
| Sorbitol | 5.000 |
| Ethyl alcohol | 15.000 |
| !-Menthol | 0.050 |
| Flavoring agent | 0.040 |
| Saccharin sodium | 0.100 |
| Water | Balance |
| TOTAL | 100.000 |

Mouth wash-Formulation C

| MATERIAL | WEIGHT % |
| --- | --- |
| Polyphenol extract-I | 0.001 |
| Trihydroxybenzoate derivatives | 0.250 |
| Sodium lauryl sulfate | 0.800 |
| Glycerine | 7.000 |
| Sorbitol | 5.000 |
| Ethyl alcohol | 15.000 |
| !-Menthol | 0.050 |
| Flavoring agent | 0.040 |
| Saccharin sodium | 0.100 |
| Water | Balance |
| TOTAL | 100.000 |

Mouth wash-Formulation D

| MATERIAL | WEIGHT % |
| --- | --- |
| Polyphenol extract-I | 0.100 |
| Trihydroxybenzoate derivatives | 0.050 |
| Sodium lauryl sulfate | 0.800 |
| Glycerine | 7.000 |
| Sorbitol | 5.000 |
| Ethyl alcohol | 15.000 |
| !-Menthol | 0.050 |
| Flavoring agent | 0.040 |
| Saccharin sodium | 0.100 |
| Water | Balance |
| TOTAL | 100.000 |

The examples described herewith are intended to demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 4

Method of Treatment

The effectiveness of the compositions of the present invention for improvement of oral health can be tested by measuring plaque accumulation over a period of time. The experiments can be conducted as follows:

A study can be carried to test the effect of a new formulation of a toothpaste containing trihydroxybenzoate derivatives on dental plaque formation. Slurries of the toothpastes being tested are prepared and used as rinses, with subjects abstaining from mechanical plaque control for 4 days. The slurry method is used because mechanical plaque control alone, performed by a skilled person, would reduce dental plaque formation, with or without the use of a toothpaste or antibacterial agent. A mouthwash formulation containing 0.5 wt. % of Oolong tea extract is chosen as a positive control.

Subject Volunteers participating in the study are non-smokers, in good general health and included both women and men between 20 and 55 years of age. They do not use any mouthwash or toothpaste containing Trihydroxybenzoate Derivatives of the Invention as part of their routine oral hygiene practices. The subjects may be chosen by the large amounts of plaque formed in the past. The trial is conducted over a period of several weeks, with the subjects attending a dental clinic on the morning of the first day for a prophylaxis. The subjects are then provided with one of three blinded samples to be used as a rinse on the evening of day 1; twice daily, morning and evening, for days 2, 3, 4; and once in the morning of day 5. Mechanical plaque control is not allowed during this period. On the morning of day 5, the subjects again attended the clinic, the plaque on their teeth is disclosed by the application of a dye, and a score in the range of 0-5 (where 0 was no plaque, 5 was maximum plaque) for individual teeth is determined. The teeth are then photographed and given a prophylaxis. The subjects are then allowed to resume their habitual plaque control for a week. On the first day of the third week, the whole process is repeated, with the subject receiving a different preparation to trial, and so on until all four samples have been tested. One of the randomized samples is a green tea extract mouthwash used as a control. At no time does the subject or the examiner know which preparation was being used. The three preparations are randomly distributed amongst the subjects in such a manner that all subjects use all four preparations but in varying order. The key is held in a secure location until the completion of the trial.

The samples that may be used are: (1) toothpaste of the present invention, mixed in a 15 ml slurry; (2) formulation containing 0.5 wt. % of Oolong tea extract is chosen as a positive control; and (3) 3 g of Placebo toothpaste, mixed in a 15 ml slurry. The teeth are examined after 4 days, and a dye was applied to highlight the plaque.

The experiment will show that the control mouthwash provides the anticipated level of plaque protection while preparations (1) and (2) above both perform significantly better than the placebo.

Second Trial

This trial focuses on microbiology, particularly changes/shifts in the flora. A mouthwash with the trihydroxybenzoate derivatives is administered 2× per day with 15 ml rinse solution, 1 minute rinse. Salivary microflora are analyzed post use at 0, 30 minutes, 60 minutes and 3 hours. LL-37 levels in whole saliva are measured at various time points. The panelists are instructed not to consume any food between measurements. The concentrations of LL-37 in saliva and GCF are measured. Checker board method is used for enumerating bacteria in saliva. A blood agar plate is used to measure total viable bacteria count in the saliva. This provides a measure of attachment loss. The following results are observed: a significant increase of LL-37 in saliva and GCF, a significant reduction of total viable bacterial account vs placebo, and a shift of the oral bacterial microflora.

Example 5

The effect of DDX5 on LL-37

Since DDX5 was found to be a possible receptor for 2,3,4- and 3,4,5-trihydroxybenzoic acids, and EGCG, based on the pull down assay, the engagement of DDX5 in the EGCG mediated up-regulation of LL-37 expression in human gingival epithelial cells was examined by functional genomic approaches.

1) Effects of DDX5-Specific RNA Interference (RNAi) on the EGCG-Induced LL-37 Expression in Human Gingival Epithelial Cells:

1-A) Efficacy of DDX5-Specific siRNA Sequences on the Suppression of DDX5 mRNA; Evaluation of RNAi Assay System (FIG. 3):

Confluent OBA-9 cultured in 24-well plate was reacted with three different sequences of siRNA for DDX5 which were designed and produced by a commercial service (Ambion, Austin, Tex.). As a control, scrambled siRNA sequence (Ambion) was used. Each siRNA was applied to the OBA9 cells in the mixture with liposome-based transfection reagent (DhermaFECT No.2, Thermo Scientific Dharmacon, Chicago Ill.). To confirm the efficiency of each siRNA to suppress DDX5 mRNA, total RNA was isolated from the cells after incubation with for siRNA for 24 h, followed by the RT-PCR for DDX5 mRNA. In order to examine the expression level of DDX5 protein, OBA-9 reacted with siRNA for 48 h was subjected to the Western-blot analysis. As shown in FIG. 3, both DDX5 mRNA as well as DDX5 protein was constitutively expressed in OBA9 cells. All three examined siRNA sequences for DDX5 mRNA showed remarkable suppression effects on the both expressions of DDX5 mRNA (RT-PCR) as well as DDX5 protein (Western blot). The expression of internal control l3-actin mRNA was not affected by the treatment with any siRNA. The control scrambled sequence of control siRNA (non-target siRNA) did not affect the expression of DDX5 mRNA as well as protein. These results demonstrated that mRNA DDX5-specific RNAi can suppress the expression of DDX5 protein, which is the receptor for 2,3,4-trihydroxybenzoic acid, and EGCG.

Figure 4:
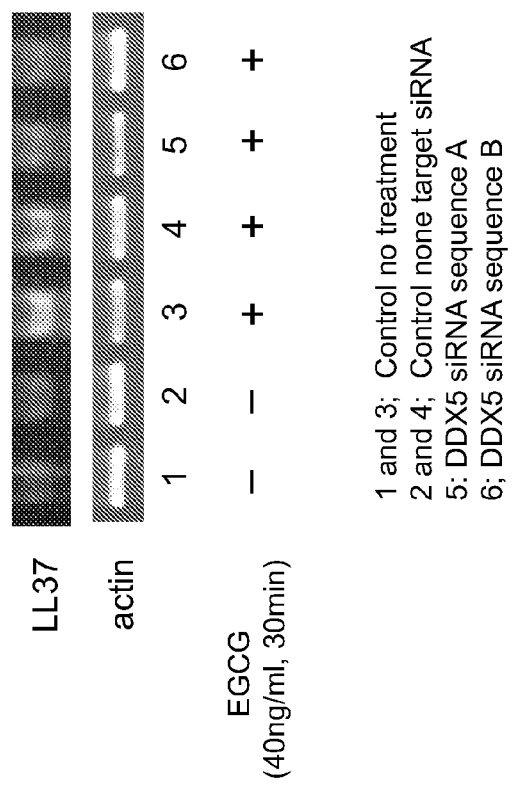
FIG. 4 is a photograph of a western blot showing the effects of DDX5 suppression on EGCG-mediated LL-37 mRNA expression in OBA9 cells (lanes: 1 and 3; Control no treatment 2 and 4; Control none target siRNA; 5: DDX5 siRNA sequence A; 6; DDX5 siRNA sequence B).

1-B) The Effect of DDX5-Specific RNAi on the EGCG-Induced LL37 mRNA Expression (FIG. 4):

After treatment of OBA9 cells with control non-target siRNA or DDX5-siRNA (#A) for 48 hours, the OBA9 cells were incubated with or without EGCG (40 ng/ml) for 30 minutes. The total RNA isolated from the OBA9 cells was subjected to RT-PCR for LL37 mRNA as well as internal control β-actin mRNA. As shown in FIG. 4, the LL37 mRNA expression induced by EGCG was inhibited by the pretreatment of OBA9 cells with DDX5-siRNA sequence #A and #B but not with control non-target siRNA, indicating that DDX5-RNAi suppress the LL-37 mRNA expression induced by EGCG.

Figure 5:
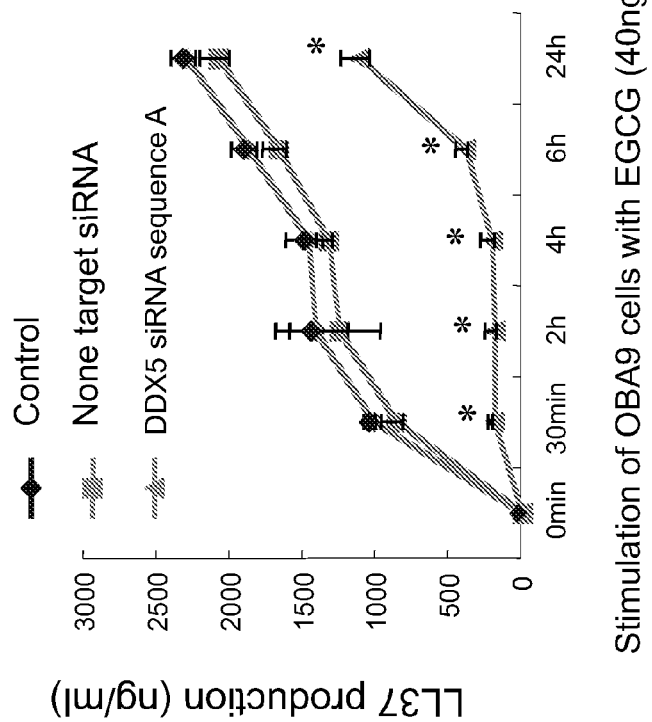
FIG. 5 is a graph showing the effects of DDX5 suppression on EGCG-mediating LL-37 expression (in ng/ml) in OBA9 cells over time.

1-C) the Effect of DDX5-Specific RNAi on the EGCG-Induced LL37 Protein Expression (FIG. 5):

The OBA9 cells which were pre-treated with control non-target siRNA or DDX5-siRNA (#A) for 48 hours, as shown in 1-B, were incubated with EGCG (40 ng/ml) for different periods from 30 min to 24 hours. The supernatant harvested from the OBA9 cell culture was subjected to ELISA for LL37 protein. As shown in FIG. 5, the LL37 expression was observed as early as 30 minutes after the EGCG stimulation and the expression level of LL37 increased in a time dependent manner. While control non-target siRNA did not affect the LL-37 expression induced by EGCG, DDX5-siRNA significantly inhibited the LL-37 expression induced by EGCG treatment for the periods from 30 min to 24 hours (*, P<0.05, Student t test). This result indicated that DDX5 is involved in the EGCG-mediated LL-37 protein expression in OBA9 cells.

2) Effects of Over Expression of DDX5 on the EGCG-Induced LL-37 Expression in Human Gingival Epithelial Cell Line, OBA9:

If DDX5 play a role as a receptor for EGCG in which action to induce LL-37 expression, over expression of DDX5 in human gingival epithelial cells (HGEC) using a molecular genetic technology should up-regulate the LL-37 expression by the EGCG-stimulated HGEC.

2-A) Development of Vector-Mediated DDX5 Over-Expression in OBA9 Cells (FIG. 6):

Open reading frame (ORF) of human DDX5 cDNA isolated from OBA9 cells was amplified and cloned into pGEM T-easy vector (Promega, Madison Wis.). In order to construct DDX5 over expression vector, the fragment of DDX5 cDNA was ligated into piRESneo3 vector (Promega). The DDX5 over expression vector was designated as pK0203, while the control empty vector was termed as pK0108.

OBA-9 was cultured as the same condition described previously. Each vector was transfected to OBA9 cells using Lipofectamine LTX (Invitrogen).

Figure 6:
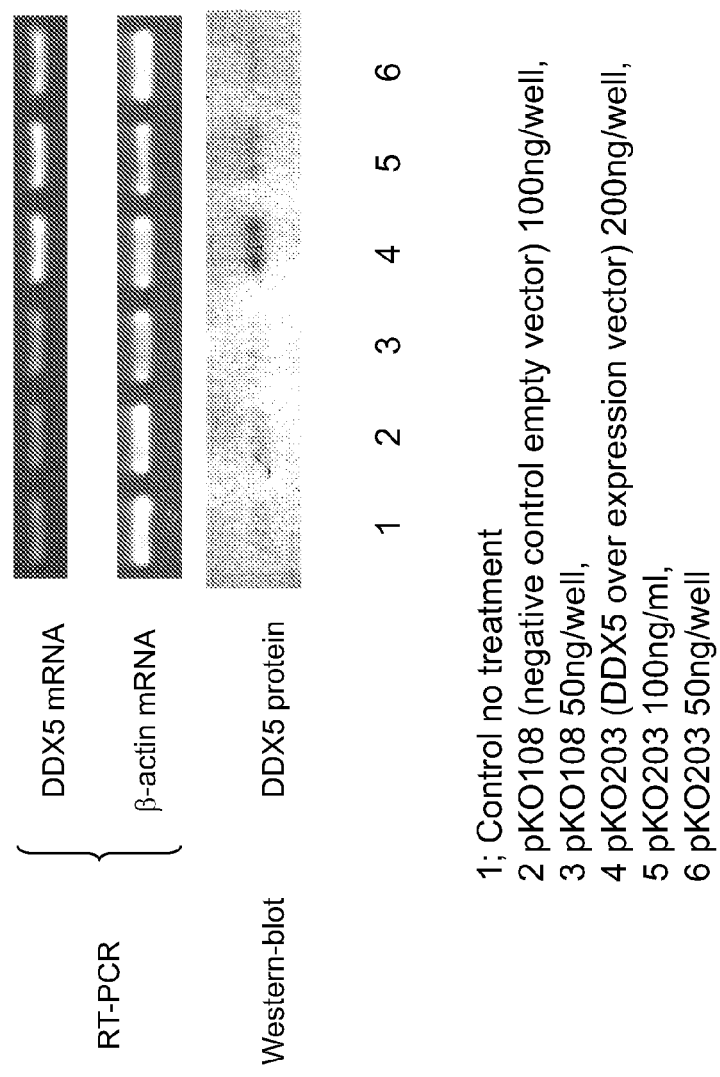
FIG. 6 is a photograph of blots showing over expression of DDX5 (by RT-PCR: DDX5 mRNA, β-actin mRNA and by western blot: DDX5 protein).

To confirm if DDX5 over expression vector (pK0203) can increase the expression of DDX5 mRNA as well as DDX5 protein, OBA9 cells received the expression vector were cultures for 24 h or 48 h, and subjected to RT-PCR and Western-blot analyses, respectively. As shown in FIG. 6, DDXS over-expression vector (pK0203) up-regulated the expression of DDX5 mRNA as well as DDX5 protein in a dose dependent manner. Contrast to pK0203, control empty vector (pK0108) did not increase the expression of DDX5 mRNA or DDX5 protein.

2-B) the Effect of DDX5 Over Expression on the Induction of LL37 Mediated by EGCG (FIG. 7):

The OBA9 cells transfected with either DDX5 over-expression vector (pK0203) or control empty vector (pKO108) were cultured for 48 h. Thereafter, the OBA9 cells were incubated with or without EGCG (40 ng/ml) for 2 hours, and the culture supernatant was subjected to ELISA for the detection of LL-37.

Figure 7:
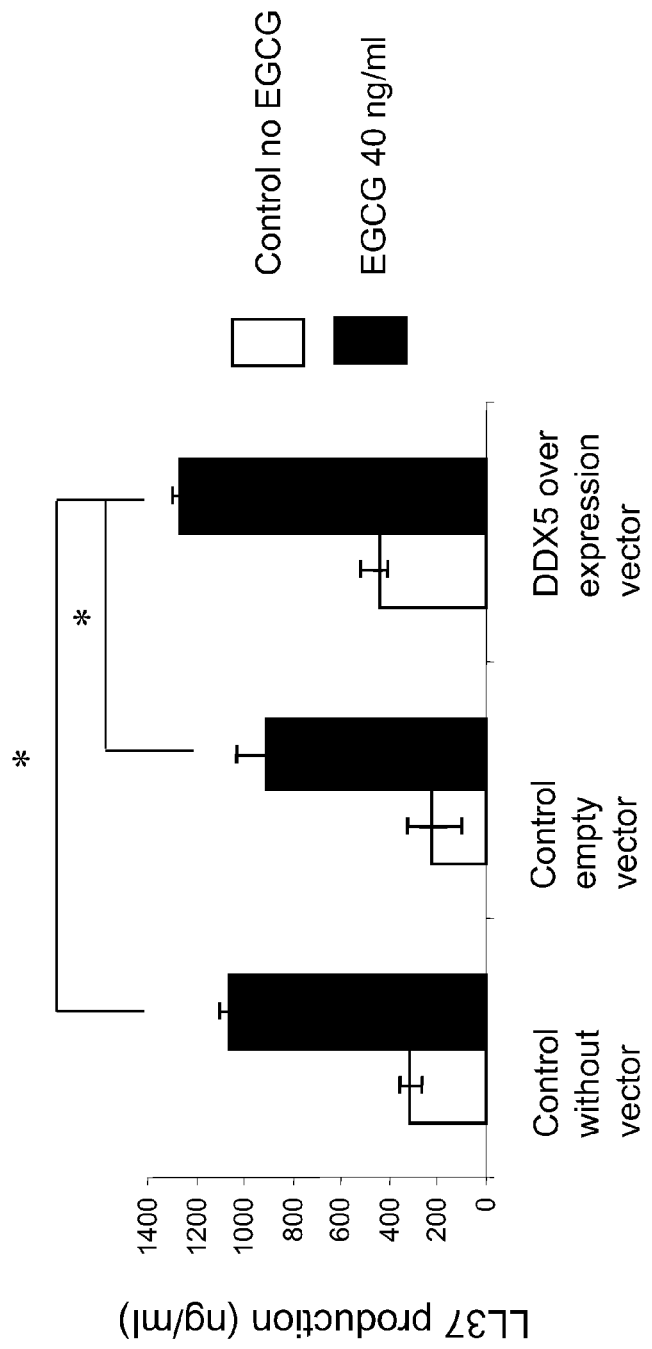
FIG. 7 is a bar graph showing the effects of DDX5 over expression on EGCG-mediated LL-37 expression (in ng/ml) in OBA9 cells.

As shown in FIG. 7, EGCG induced the LL-37 expression in all three conditions of OBA9 treatment, i.e. 1) control OBA9 received no vector, 2) OBA9 cells transfected with control empty vector (pK0108), and 3) OBA9 cells transfected with DDX5 over-expression vector (pK0203).

Most importantly, LL-37 expression induced by EGCG was significantly higher in the OBA9 cells transfected with DDX5 over-expression vector than 1) control OBA9 received no vector or 2) OBA9 cells transfected with control empty vector (pKO108) (*, P<0.05, Student t test). Therefore, this result indicated that increased amount of DDX5 can promote the EGCG-mediated LL-37 protein expression in OBA9 cells.

Based on the results obtained from loss-of-function assay using RNAi technology and gain-of-function assay using vector-based over expression, DDX5 functions as a receptor for EGCG, as well as 2,3,4- and 3,4,5-trihydroxybenzoic acids.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

The entire teachings of the following application are incorporated herein by reference: U.S. application Ser. No. 12/762,212 filed on Apr. 16, 2010, entitled "New Methods of Making An Antibody and Compositions Thereof" by Toshihisa Kawai, et al.

What is claimed is:

1. A method of treating an oral cavity disease or condition in an individual, the method comprising administering a therapeutically effective amount of one or more compounds having one or more trihydroxybenzoate moieties to the oral cavity of the individual; wherein the stimulation of the production of antimicrobial peptides occurs to thereby treat the oral cavity disease or condition in the individual.

2. The method of claim 1, wherein the oral cavity disease or condition comprises thrush, gingivitis, periodontitis, oral candidiasis, salivary diseases associated with bacterial, viral, or fungal infections; Crohn's disease, irritable bowel syndrome, ulcerative colitis, *Helicobacter pylori* caused stomach ulcer, and gastrointestinal diseases associated with mucosal bacteria.

3. The method of claim 2, wherein stimulation of the production of antimicrobial peptide reduces one or more symptoms associated with the oral cavity disease or condition.

4. A method of treating an oral cavity disease or condition in an individual, the method comprising administering a therapeutically effective amount of one or more compounds having one or more trihydroxybenzoate moieties to the oral cavity of the individual; whereby oral bacteria are reduced or inhibited to thereby treat the oral cavity disease or condition in the individual.

5. The method according to claim 4, wherein a level of antimicrobial LL-37 peptides in the oral cavity is increased, as compared to a level of antimicrobial LL-37 peptides prior to administration of the oral care composition.

* * * * *

SEQUENCE LISTING

```
<160> NUMBER OF SEQ ID NOS: 7

<210> SEQ ID NO 1
<211> LENGTH: 615
<212> TYPE: PRT
<213> ORGANISM: Homo sapiens

<400> SEQUENCE: 1

Met Ser Gly Tyr Ser Ser Asp Arg Asp Arg Gly Arg Asp Arg Gly Phe
1               5                  10                  15

Gly Ala Pro Arg Phe Gly Gly Ser Arg Ala Gly Pro Leu Ser Gly Lys
            20                  25                  30

Lys Phe Gly Asn Pro Gly Glu Lys Leu Val Lys Lys Lys Trp Asn Leu
        35                  40                  45

Asp Glu Leu Pro Lys Phe Glu Lys Asn Phe Tyr Gln Glu His Pro Asp
    50                  55                  60

Leu Ala Arg Arg Thr Ala Gln Glu Val Glu Thr Tyr Arg Arg Ser Lys
65                  70                  75                  80

Glu Ile Thr Val Arg Gly His Asn Cys Pro Lys Pro Val Leu Asn Phe
                85                  90                  95

Tyr Glu Ala Asn Phe Pro Ala Asn Val Met Asp Val Ile Ala Arg Gln
            100                 105                 110

Asn Phe Thr Glu Pro Thr Ala Ile Gln Ala Gln Gly Trp Pro Val Ala
        115                 120                 125
```

-continued

Leu Ser Gly Leu Asp Met Val Gly Val Ala Gln Thr Gly Ser Gly Lys
130                 135                 140

Thr Leu Ser Tyr Leu Leu Pro Ala Ile Val His Ile Asn His Gln Pro
145                 150                 155                 160

Phe Leu Glu Arg Gly Asp Gly Pro Ile Cys Leu Val Leu Ala Pro Thr
            165                 170                 175

Arg Glu Leu Ala Gln Gln Val Gln Gln Val Ala Glu Tyr Cys Arg
            180                 185                 190

Ala Cys Arg Leu Lys Ser Thr Cys Ile Tyr Gly Gly Ala Pro Lys Gly
            195                 200                 205

Pro Gln Ile Arg Asp Leu Glu Arg Gly Val Glu Ile Cys Ile Ala Thr
210                 215                 220

Pro Gly Arg Leu Ile Asp Phe Leu Glu Cys Gly Lys Thr Asn Leu Arg
225                 230                 235                 240

Arg Thr Thr Tyr Leu Val Leu Asp Glu Ala Asp Arg Met Leu Asp Met
                245                 250                 255

Gly Phe Glu Pro Gln Ile Arg Lys Ile Val Asp Gln Ile Arg Pro Asp
            260                 265                 270

Arg Gln Thr Leu Met Trp Ser Ala Thr Trp Pro Lys Glu Val Arg Gln
            275                 280                 285

Leu Ala Glu Asp Phe Leu Lys Asp Tyr Ile His Ile Asn Ile Gly Ala
290                 295                 300

Leu Glu Leu Ser Ala Asn His Asn Ile Leu Gln Ile Val Asp Val Cys
305                 310                 315                 320

His Asp Val Glu Lys Asp Glu Lys Leu Ile Arg Leu Met Glu Glu Ile
                325                 330                 335

Met Ser Glu Lys Glu Asn Lys Thr Ile Val Phe Val Glu Thr Lys Arg
            340                 345                 350

Arg Cys Asp Glu Leu Thr Arg Lys Met Arg Arg Asp Gly Trp Pro Ala
            355                 360                 365

Met Gly Ile His Gly Asp Lys Ser Gln Gln Glu Arg Asp Trp Val Leu
370                 375                 380

Asn Glu Phe Lys His Gly Lys Ala Pro Ile Leu Ile Ala Thr Asp Val
385                 390                 395                 400

Ala Ser Arg Gly Leu Asp Val Glu Asp Val Lys Phe Val Ile Asn Tyr
                405                 410                 415

Asp Tyr Pro Asn Ser Ser Glu Asp Tyr Ile His Arg Ile Gly Arg Thr
            420                 425                 430

Ala Arg Ser Thr Lys Thr Gly Thr Ala Tyr Thr Phe Phe Thr Pro Asn
            435                 440                 445

Asn Ile Lys Gln Val Ser Asp Leu Ile Ser Val Leu Arg Glu Ala Asn
450                 455                 460

Gln Ala Ile Asn Pro Lys Leu Leu Gln Leu Val Glu Asp Arg Gly Ser
465                 470                 475                 480

Gly Arg Ser Arg Gly Arg Gly Met Lys Asp Asp Arg Arg Asp Arg
                485                 490                 495

Tyr Ser Ala Gly Lys Arg Gly Phe Asn Thr Phe Arg Asp Arg Glu
            500                 505                 510

Asn Tyr Asp Arg Gly Tyr Ser Ser Leu Leu Lys Arg Asp Phe Gly Ala
            515                 520                 525

Lys Thr Gln Asn Gly Val Tyr Ser Ala Ala Asn Tyr Thr Asn Gly Ser
530                 535                 540

```
Phe Gly Ser Asn Phe Val Ser Ala Gly Ile Gln Thr Ser Phe Arg Thr
545                 550                 555                 560

Gly Asn Pro Thr Gly Thr Tyr Gln Asn Gly Tyr Asp Ser Thr Gln Gln
            565                 570                 575

Tyr Gly Ser Asn Val Pro Asn Met His Asn Gly Met Asn Gln Gln Ala
        580                 585                 590

Tyr Ala Tyr Pro Ala Thr Ala Ala Ala Pro Met Ile Gly Tyr Pro Met
    595                 600                 605

Pro Thr Gly Tyr Ser Gln Leu
    610                 615

<210> SEQ ID NO 2
<211> LENGTH: 21
<212> TYPE: DNA
<213> ORGANISM: Homo sapiens

<400> SEQUENCE: 2
ccugauaggc aaacucuaat t                                          21

<210> SEQ ID NO 3
<211> LENGTH: 21
<212> TYPE: DNA
<213> ORGANISM: Homo sapiens

<400> SEQUENCE: 3
uuagaguuug ccuaucaggt c                                          21

<210> SEQ ID NO 4
<211> LENGTH: 21
<212> TYPE: DNA
<213> ORGANISM: Homo sapiens

<400> SEQUENCE: 4
ggcgaugggc cuauuuguut t                                          21

<210> SEQ ID NO 5
<211> LENGTH: 21
<212> TYPE: DNA
<213> ORGANISM: Homo sapiens

<400> SEQUENCE: 5
aacaaauagg cccaucgcct c                                          21

<210> SEQ ID NO 6
<211> LENGTH: 21
<212> TYPE: DNA
<213> ORGANISM: Homo sapiens

<400> SEQUENCE: 6
ccaaaagaag augugaugat t                                          21

<210> SEQ ID NO 7
<211> LENGTH: 21
<212> TYPE: DNA
<213> ORGANISM: Homo sapiens

<400> SEQUENCE: 7
ucaucacauc uucuuuuggt t                                          21
```